US012702385B2

(12) United States Patent
Schwenke et al.

(10) Patent No.: US 12,702,385 B2
(45) Date of Patent: Aug. 11, 2026

(54) DERIVING TISSUE DAMAGE ESTIMATIONS FROM ULTRASOUND IMAGES DURING THERMAL ABLATION

(71) Applicant: TECHSOMED MEDICAL TECHNOLOGIES LTD, Rehovot (IL)

(72) Inventors: Michael Schwenke, Lilienthal (DE); Yehonatan Ben David, Ramat Gan (IL); Tom Edlund, Neve Shalom (IL)

(73) Assignee: TECHSOMED MEDICAL TECHNOLOGIES LTD, Rehovot (IL)

( * ) Notice: Subject to any disclaimer, the term of this patent is extended or adjusted under 35 U.S.C. 154(b) by 0 days.

(21) Appl. No.: 18/899,359

(22) Filed: Sep. 27, 2024

(65) Prior Publication Data

US 2025/0107780 A1 Apr. 3, 2025

Related U.S. Application Data

(60) Provisional application No. 63/586,086, filed on Sep. 28, 2023.

(51) Int. Cl.
*A61B 8/00* (2006.01)
*A61B 34/10* (2016.01)
(Continued)

(52) U.S. Cl.
CPC ............ *A61B 8/5215* (2013.01); *A61B 34/10* (2016.02); *G06T 7/0014* (2013.01); *G06T 7/10* (2017.01);
(Continued)

(58) Field of Classification Search
CPC . A61B 8/5215; A61B 34/10; A61B 2034/104; A61B 2034/105;
(Continued)

(56) References Cited

U.S. PATENT DOCUMENTS 11,123,046 B1 * 9/2021 Zohar .................. A61B 8/0891
2024/0206907 A1 * 6/2024 Wu .................... A61B 17/3403

FOREIGN PATENT DOCUMENTS

WO WO 2021/224921 11/2021

OTHER PUBLICATIONS

Ronneberger et al; U-Net: Convolutional Networks for Biomedical Image Segmentation, Computer Science Department and BIOSS Centre for Biological Signalling Studies, University of Freiburg, Germany, May 18, 2015.

(Continued)

*Primary Examiner* — Patricia J Park
(74) *Attorney, Agent, or Firm* — PEARL COHEN ZEDEK LATZER BARATZ LLP

(57) ABSTRACT

Ultrasound (US) modules and methods in US image-guided systems for thermal ablation are provided, which utilize regular two-dimensional (2D) B mode US images to evaluate in real-time the damage achieved by the thermal ablation, including the prediction of tissue damage immediately after completion of the thermal ablation procedure, as well as the expected damage after 24 hours. Three-dimensional (3D) biotrace map (BTM) representation(s) may be constructed from the received US images by applying deep neural networks (DNN) to segment tissue damage in US frames, and present the damage to the user in 3D and/or in virtual sections through the BTM representation(s). Using regular 2D US probes allows much flexibility in operating the US probe and imaging the target successfully, while the construction of the 3D BTM representation(s) enables accumulating, updating and analyzing the volume data to provide a full and updating representation of the ablation procedure.

22 Claims, 14 Drawing Sheets
(5 of 14 Drawing Sheet(s) Filed in Color)

(51) Int. Cl.
*G06T 7/00* (2017.01)
*G06T 7/10* (2017.01)

(52) U.S. Cl.
CPC ... *A61B 2034/104* (2016.02); *A61B 2034/105* (2016.02); *A61B 2034/107* (2016.02); *G06T 2207/10132* (2013.01); *G06T 2207/20084* (2013.01); *G06T 2207/20172* (2013.01)

(58) Field of Classification Search
CPC ... A61B 2034/107; G06T 7/10; G06T 7/0014; G06T 2207/10132; G06T 2207/20084; G06T 2207/20172
See application file for complete search history.

(56) References Cited

OTHER PUBLICATIONS

Yuni K Dewaraja et al; Intra- and Inter-operator variability in manual tumor segmentation: Impact on radionuclide therapy dosimetry; Research Article, Research Gate; Mar. 9, 2022.

* cited by examiner

Ultrasound module (B mode)
65
60
85
86
305
310
86
70
82
83

Ultrasound module (B mode)
65
60
85
86
305
305
86
70
82
83

Ultrasound module (B mode)
85
Z
X
Y
80
82
70
83

DERIVING TISSUE DAMAGE ESTIMATIONS FROM ULTRASOUND IMAGES DURING THERMAL ABLATION

CROSS REFERENCE TO RELATED APPLICATIONS

This application claims the benefit of U.S. Provisional Application No. 63/586,086, filed on Sep. 28, 2024, which is incorporated herein by reference in its entirety.

BACKGROUND OF THE INVENTION

1. Technical Field

The present invention relates to the field of ultrasound image-guided systems for thermal ablation, and more particularly, to the derivation of tissue damage estimations during thermal ablation.

2. Discussion of Related Art

U.S. Pat. No. 11,123,046 and WIPO Publication No. 2021224921, which are incorporated herein by reference in their entirety, teach systems, displays and methods for performing ultrasound image registration and for using ultrasound images to guide thermal ablation. Registration is carried out by correlating sequential ultrasound images, identifying key frames from the correlation values, identifying periodic change(s) corresponding to breathing and heart beating, and correlating pixels in sequential key frames that have a same phase with respect to the identifying periodic change(s). Based on the registration, the start of ablation is detected, bubbles formed in the ablation procedure are identified and their movements are followed—all using B-mode ultrasound images only. Using the identified bubbles, the thermally damaged tissue region is demarcated and provided in real-time at an accuracy similar to prior art post-ablation results. It is challenging to derive real-time damage evaluating data for various reasons, including the dynamic generation of gas bubbles during ablation which may preclude obtaining acoustic images during the process, patient characteristics (e.g., fat may make imaging difficult) and tumor location (e.g., close to shadowing elements such as ribs).

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides an ultrasound module in an ultrasound image-guided system for thermal ablation, the ultrasound module configured to receive at least one B-mode ultrasound (US) tissue image during the thermal ablation, and to derive therefrom a biotrace map (BTM) that provides a tissue damage assessment—by applying at least one deep neural network (DNN) to segment tissue damage in the at least one received tissue image to yield the BTM.

One aspect of the present invention provides a method comprising deriving a biotrace map (BTM) during thermal ablation from at least one B-mode ultrasound (US) tissue image received during the thermal ablation by applying at least one deep neural network (DNN) to segment tissue damage in the at least one received ultrasound tissue image.

One aspect of the present invention provides a computer program product comprising a non-transitory computer readable storage medium having computer readable program embodied therewith, the computer readable program comprising: computer readable program configured to derive a biotrace map (BTM) during thermal ablation from at least one B-mode ultrasound (US) tissue image received during the thermal ablation by applying at least one deep neural network (DNN) to segment tissue damage in the at least one received ultrasound tissue image.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout. The patent or application file contains at least one drawing executed in color. Copies of this patent or patent application publication with color drawing(s) will be provided by the Office upon request and payment of the necessary fee. In the accompanying drawings.

Figure 1:
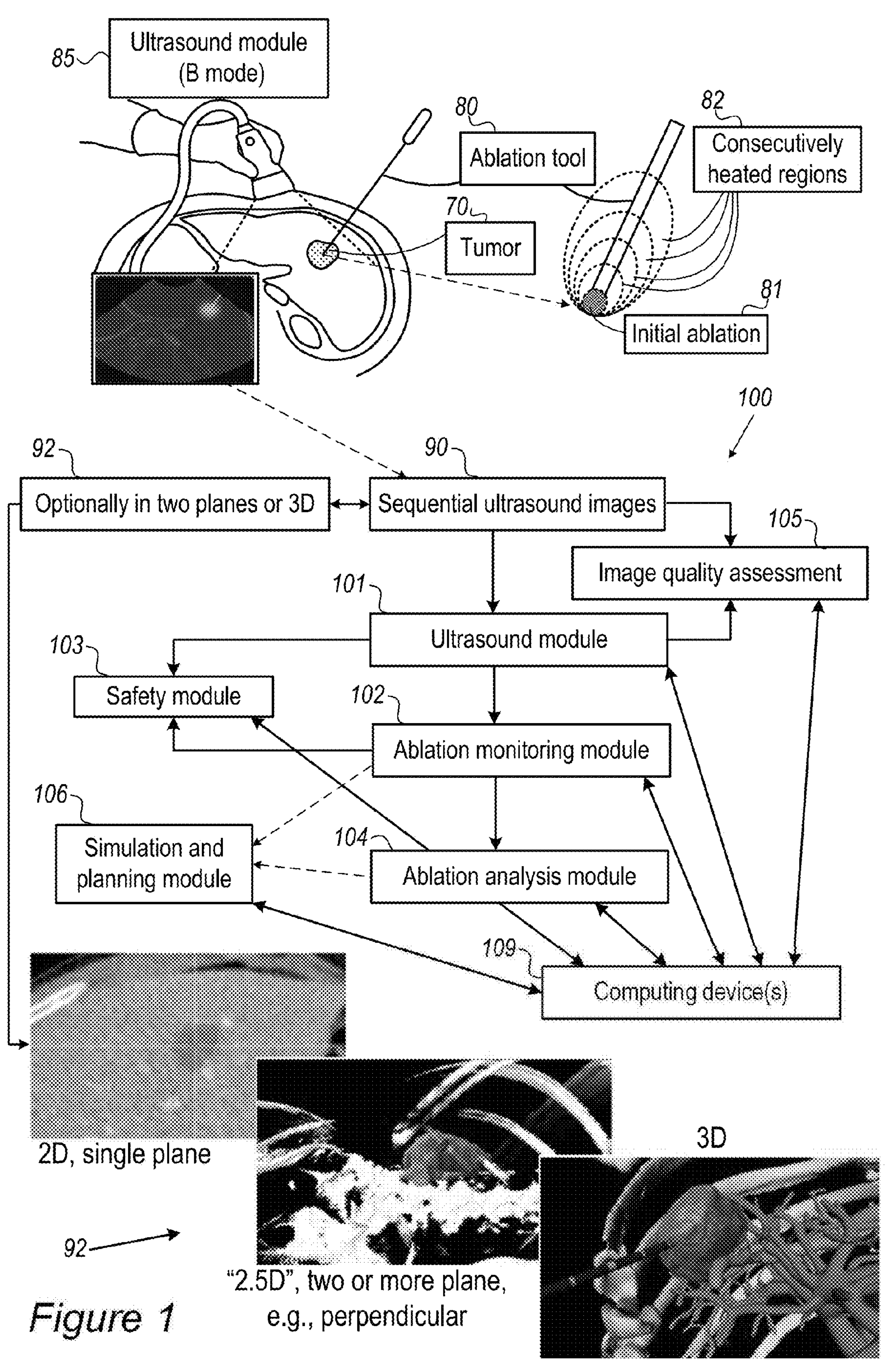
FIG. 1 is a high-level schematic illustration of an ultrasound image-guided system for performing a thermal ablation procedure, according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well-known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein are for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing", "deriving" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

Embodiments of the present invention provide efficient and economical methods and mechanisms for detecting and/or segmenting tissue damage in ultrasound (US) images during thermal ablation and thereby provide improvements to the technological field of monitoring such medical procedures.

Ultrasound (US) modules and methods in US image-guided systems for thermal ablation are provided, which utilize regular two-dimensional (2D) B mode US images to evaluate in real-time the damage achieved by the thermal ablation, including the prediction of tissue damage immediately after completion of the thermal ablation procedure (e.g., as would be detected by post ablation contrast enhanced CT (CECT), as well as the expected damage after 24 hours. Three-dimensional (3D) biotrace map (BTM) representation(s) may be constructed from the received US images by applying deep neural networks (DNN) to segment tissue damage in US frames, and present the damage to the user in 3D and/or in virtual sections through the BTM representation(s). Using regular 2D US probes allows much flexibility in operating the US probe and imaging the target successfully, while the construction of the 3D BTM representation(s) enables accumulating, updating and analyzing the volume data to provide a full and updating representation of the ablation procedure.

An ultrasound module in an ultrasound image-guided system for thermal ablation is provided, alongside methods of deriving a tissue damage map (TDM) during thermal ablation and corresponding computer program products. The TDM is derived (e.g., detected and/or segmented) by applying a deep neural network (DNN) to segment tissue damage of a received ablation frame to yield the TDM. In the present disclosure, the term BTM—biotrace map is used synonymously to the term TDM.

TDMs/BTMs disclosed herein, may be derived to yield 2D (two dimensional) representations of the ablated tissue, 2.5D ("two and a half dimensional) representations referring to the representation of the ablated tissue in two or more planes, e.g., perpendicular planes, and/or a 3D (three dimensional) representation of the ablated tissue, as described herein.

In various embodiments, disclosed methods, US modules and systems utilize 2D US sweeping with tracking (e.g., electromagnetic and/or optical tracking) of the ultrasound probe—to reconstruct the 3D US volume from the US images before ablation (possibly with inserted needle) and to reconstruct the 3D US model (e.g., before applying the DNNs, or after applying the DNNs—yielding the BTM representation) during ablation, replacing existing data with new frames as the procedure advances. The ablation needle may be identified in the 3D US model (manually or automatically) and the 3D US model may be fused with pre-therapy data like CT (computer tomography) and/or MR (magnetic resonance) images with anatomical structures. The estimation of ablation damage to derive a 3D BTM (biotrace map, also termed tissue damage map—TDM) may be carried out by using a 2D-DNN on each input US frame directly and/or by using a 2D-DNN on virtual 2D US reconstructions (derived from the generated 3D US model), which may be rotating around the target area and cutting centered through target. The prediction based on the DNNs may be combined to yield a joint 3D BTM estimate, and a damage model may be used to integrate the BTM prediction over space and time to yield a final damage estimate.

In some embodiments, 3D DNN(s) may be applied to US images to generate the 3D BTM. For example, a full 3D DNN may be applied to 3D US volume or model to derive 3D BTM representations.

In some embodiments, a large number of virtual 2D US images may be derived from the 3D US model, e.g., a few tens of images centered on the ablation target and rotating around it to cover the volume of the treated area, and DNN may be applied to all virtual images to evaluate the created ablation damage as the 3D BTM.

In some embodiments, virtual 2D US image(s) may be derived with respect to user indication and/or to optimize target visibility and damage estimation in addition to the received at least one B-mode US image. For example, a multitude of virtual 2D sections may be derived from the 3D US representation (e.g., 3D BTM representations) to optimize target visibility and damage estimation in addition to the direct 2D US input stream. Prior to the ablation procedure, virtual 2D sections may be derived from the 3D US reference model to enhance planning the ablation procedure.

The ultrasound images may be B-mode images, the images may be registered or unregistered and may include reference frame(s), e.g., acquired prior to ablation start, and the DNNs may comprise backbone DNN(s) for feature extraction and head DNN(s) for damage detection and/or segmentation based on the extracted features. The DNNs may have a U-shaped network (UNet) architecture, as a non-limiting example. The TDMs may be enhanced by application of shadow compensation and post processing, and/or by accumulating TDMs, e.g., with respect to damage thresholds for specific frames to yield a final TDM segmentation. As a non-limiting example, the TDM may be derived by selecting a reference frame from received B-mode ultrasound images of undamaged tissue, registering consecutive tissue ultrasound images, received during the ablation procedure, with respect to the reference frame, deriving an initial TDM using a weighted average of three U-shaped networks applied, respectively, to the reference frame, the registered frame and a difference between them, wherein the U-shaped networks are trained using a weighted sum of at least two loss functions (e.g., Binary Cross Entropy and Boundary-based Loss functions as non-limiting examples), and applying shadow compensation and post processing to the initial TDM to yield the final TDM segmentation.

To yield 3D representations, sweeping of the US probe across the region of interest (ROI) surrounding the location of ablation may be used to derive the 3D representations, from which 2D cross sections may be derived, as described herein. In various embodiments, multiple US images may be used to construct a reference 3D US volume from the pre-ablation frames. During the ablation process, reference 3D US volume and/or a representative pre-ablation frame and/or a virtual section through the reference 3D representation may be used for comparison with some or each received ablation US image to derive the damage estimation. Correspondingly, DNNs may also be 3D DNN, for example include 3D DNNs with U-shaped network (UNet) architectures. 2D or 3D UNet DNNs may receive respective 2D and/or 3D input by changing the 2D and/or 3D convolution layers respectively.

FIG. 1 is a high-level schematic illustration of an ultrasound image-guided system 100 for performing a thermal ablation procedure, according to some embodiments of the invention. For example, FIG. 1 schematically illustrates using a thermal ablation tool 80, e.g., using RF (radiofrequency), MW (microwave) or possibly laser energy, to ablate tissue 70 such as a tumor, e.g., in the liver. The thermal ablation procedure is monitored in real-time by an ultrasound module 85, operating in B mode, which provides sequential ultrasound images 90 which are used by ultrasound image-guided system 100 to monitor the thermal ablation procedure, e.g., identifying ablated tissue, distinguishing targeted tissue 70 from surrounding tissue, providing feedback concerning the progression of the thermal ablation procedure, indicating the extent of removed targeted tissue 70, alerting concerning ablated surrounding tissue and/or safety boundaries being approached, as well as providing real-time assessment of the success of the thermal ablation procedure in removing targeted tissue 70. Sequential ultrasound images 90 may be used to derive a two-dimensional (2D) representation of the ablated tissue, a representation of the ablated tissue in two or more planes, e.g., perpendicular planes (termed "2.5D"), and/or a three-dimensional (3D) representation of the ablated tissue—as illustrated schematically and denoted 92. It is noted that 2D evaluation requires placing the US probe still at one position, while the 2.5D evaluation is similar to the 2D evaluation, but taken at two (e.g., perpendicular, or otherwise tilted with respect to each other) plane slices. The 3D evaluation allows for, and benefits from repositioning the (2D) US probe during the thermal ablation procedure, as typically carried out by the user (e.g., physician), and provides a 3D model from which virtual 2D slices may be derived at the user's request and/or in relation to the 3D geometry of the ablated region. Advantageously, deriving and using the virtual US slices(s) may overcome inherent limitations of currently used US sweeping techniques by optimizing the visibility of relevant or crucial tissue structures as well as providing the optimal viewing direction of the target with respect to considerations related to the ablation procedure. It is noted that evaluations may be used from both 2D (or 2.5D) reconstructions and from the 3D reconstruction (or from one or more virtual planes thereof, as disclosed below) —to validate and to optimize the final damage evaluation.

It is noted that in current technology, a time period of about a day is required to pass before reliable imaging can be used to determine the extent of ablated targeted tissue 70 and damage to surrounding tissue, by then another procedure should be undertaken to correct for any deficiencies. In disclosed embodiments, the provided feedback is immediate and allows for optimization of the thermal ablation procedure during its execution. Disclosed algorithms provide real-time predictions concerning the expected full scope of ablation in 24/48 h—which were found to be reliable and accurate, as described herein.

In various embodiments, ultrasound image-guided system 100 for thermal ablation includes ultrasound module 101 configured to provide continuity and spatial orientation from incoming sequential ultrasound images 90 and ablation monitoring module 102 configured to detect and monitor the thermal ablation procedure. Additional modules may be used to provide safety alerts (e.g., safety module 103), assess image quality (e.g., image quality assessment module 105) and possibly improve image quality, provide reports concerning the thermal ablation procedure after it is finished, derive additional data and analysis (e.g., ablation analysis module 104) etc., and to plan the thermal ablation procedure (e.g., simulation and planning module 106).

In the following, first the case of 2D tissue damage analysis is described, followed by a description of "2.5D" tissue damage analysis and then by a description of full 3D tissue damage analysis. Predictions provided by disclosed TDM/BTM include the prediction of tissue damage immediately after completion of the thermal ablation procedure (e.g., as would be detected by post ablation contrast enhanced CT (CECT), as well as the expected damage after 24 or 48 hours, as would be detected by CT or other imaging methods.

Figure 2A:
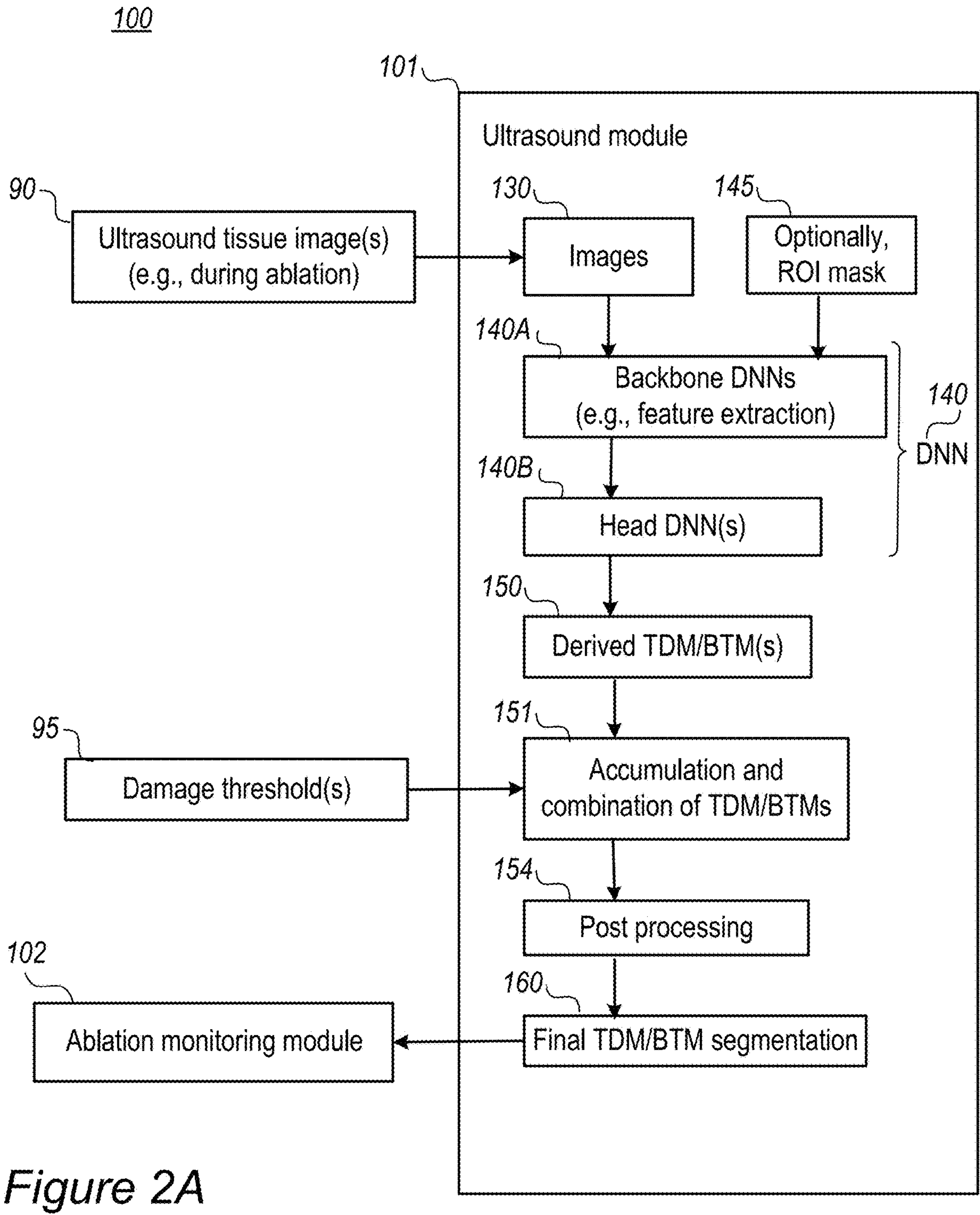
FIGS. 2A and 2B are high-level schematic block diagrams of non-limiting examples for an ultrasound module, according to some embodiments of the invention.
Figure 2B:
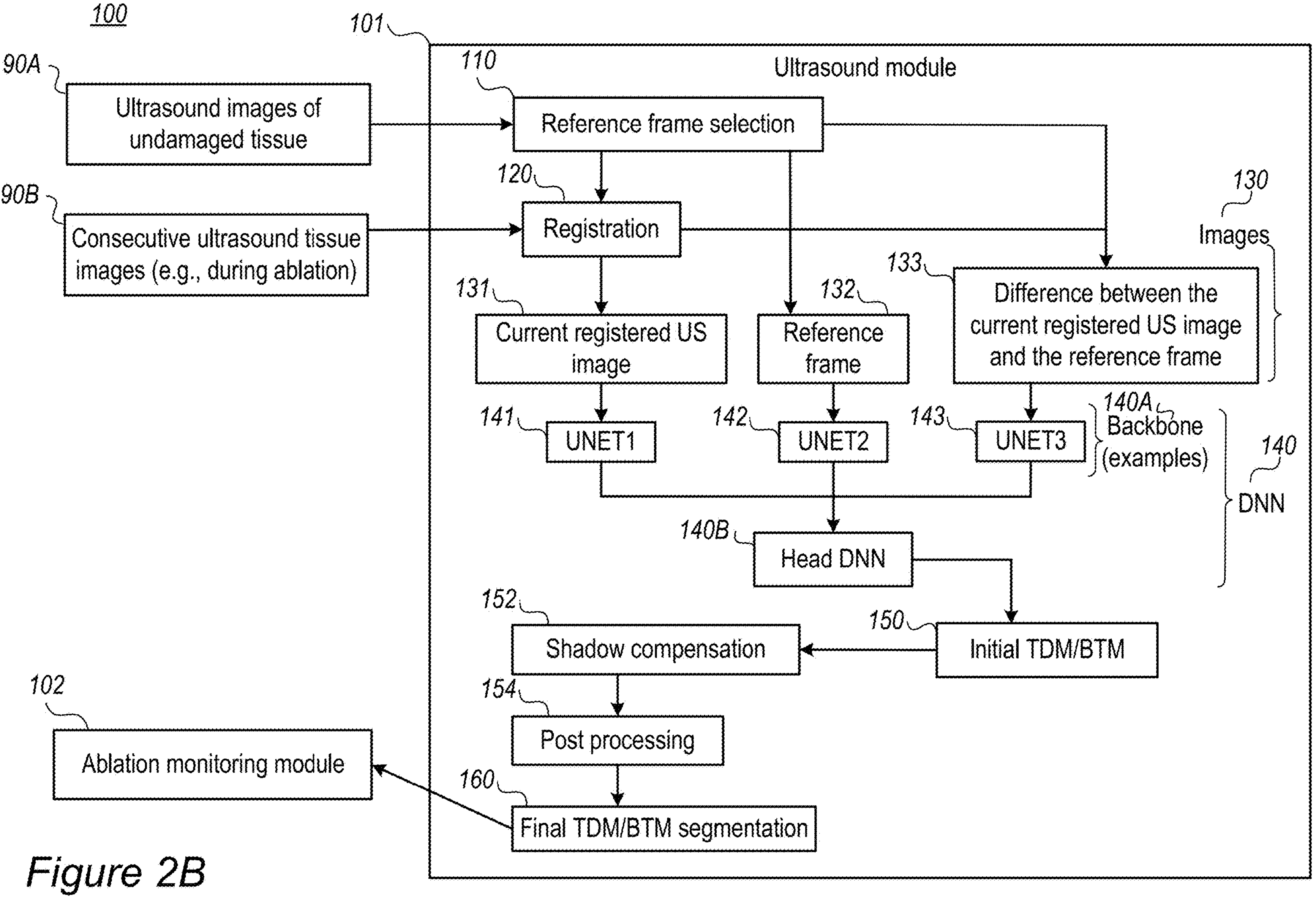

FIGS. 2A and 2B are high-level schematic block diagrams of non-limiting examples for an ultrasound module, according to some embodiments of the invention. In various embodiments, ultrasound module 101 for TDM/BTM segmentation and/or detection may be configured to receive at least one tissue image 90 during the thermal ablation (for example, one or more images of damaged tissue, e.g., received during the thermal ablation, one or more images of undamaged tissue) and to derive therefrom TDM/BTM 150 by applying a deep neural network (DNN) 140 to segment tissue damage in the at least one received tissue image to yield the TDM/BTM. DNN 140 may be configured to detect and/or segment tissue damage through TDM/BTM 150. In various embodiments, DNN(s) 140 may be applied to any of: one or more 2D US image, one or more virtual US images derived from the 3D model disclosed herein and/or the 3D model itself, as well as combinations of these data. The DNN estimates may then be aggregated to yield the 3D BTM as map of the damaged tissue regions, including estimations of the level and/or likelihood of damage (e.g., per pixel, per voxel, per region and/or in total). The estimated damage may be calculated with weights assigned to different pixels, voxels or regions, e.g., according to their distance from the needle tip and/or according to the time elapsed since the start of ablation. In some embodiments, the 3D BTM representation may be updated with derived data concerning heat propagation with respect to the needle position (e.g., according to characteristics of the ablation device) to improve the accuracy and robustness of the BTM algorithm.

In the schematic illustration of FIG. 2A, tissue image(s) 90 may be received as image 130, handled by DNN 140 to yield, e.g., feature extraction by backbone DNN(s) 140A and consecutively damage detection and/or segmentation by head DNN(s) 140B, which may be used to derive TDM/BTM 150. In certain embodiments, head DNN(s) 140B may comprise a small network configured to learn the optimal combination of the outputs of backbone networks 140A and possible use the outputs to augment derived TDM/BTMs 150. Multiple TDM/BTMs 150 may be derived, accumulated and combined (denoted as stage 151), e.g., with respect to defined damaged threshold(s) 95. The combined TDM/BTMs may be post-processed 154 to yield one or more final TDM/BTMs 160 that are provided to ablation monitoring module with system 100.

In certain embodiments, ultrasound module 101 may be configured to receive at least one reference image and/or at least one image of undamaged tissue and derive TDM/BTM 150 with respect thereto and tissue images 90, e.g., using comparison and registration. In a non-limiting example, DNN 140 may receive as input (i) an input frame only (registered or unregistered), (ii) an input frame and a reference frame (see, e.g., FIG. 2B), or (iii) any combination of one or more input frame and one or more reference frame (e.g., for one or more subregions of the imaged region).

In various embodiments, DNN 140 may comprise one or more DNNs having a U-shaped network (UNet) architecture, e.g., as backbone DNN 140A. The DNN's UNet architecture may be customized to include multiple UNet sub-networks (see example below). The DNN(s) may be applied to segment tissue damage of a registered ablation frame and yield the TDM/BTM.

In some embodiments, an ROI mask 145 may be applied and used to define specific regions in which DNN(s) 140 are applied, to improve the accuracy and robustness of the disclosed algorithms. For example, the ROI mask may be derived from the detected (or inputted) needle location and/or from specifications related to the ablation tool, and/or from information derived during the derivation of the TDM/BTM representations.

In non-limiting example presented in FIG. 2B, ultrasound module 101 may be configured to receive images of undamaged tissue 90A and consecutively receive tissue images 90B during the thermal ablation, and to derive therefrom the TDM/BTM by: (i) selecting a reference frame 110 from received images 90A of undamaged tissue, (ii) registering 120 the consecutive tissue images with respect to reference frame 110—to yield registered frame(s), (iii) deriving an initial TDM/BTM 150 using head DNN 140B or, in a non-limiting example, a weighted average of three U-shaped networks 141, 142, 143 (as a non-limiting embodiment of backbone DNN 140A) applied, respectively, to registered frame 131, reference frame 110 (denoted 132 when used to apply UNET2 142 thereto), and a difference between them 133, wherein the U-shaped networks 141, 142, 143 are trained using a weighted sum of at least two loss functions (e.g., Binary Cross Entropy and Boundary-based Loss function), and (iv) applying shadow compensation 152 (e.g., applying shadow detection and processing) and post processing 154 (e.g., combining information from computer vision algorithms) to initial TDM/BTM 150 to yield a final TDM/BTM segmentation 160 that can be used, e.g., for monitoring the ablation process. It is noted that UNET1, 2, 3 are U-shaped networks optionally, as backbone DNNs 140A), which are modified fully convolutional neural networks (CNN), described in Ronneberger et al. 2015 (U-Net: Convolutional Networks for Biomedical Image Segmentation, arXiv:1505.04597).

The weights for training the networks were optimized by deriving them for a part of the data set (related to different locations and different imaging settings), and testing the resulting networks on cases that were not used for the training (excluded from the used part of the data set) in order to avoid overfitting. The optimized weights were derived from recurrent application of the derivation for different parts of the dataset.

Different types of loss functions may be used for the training, in some examples, Binary Cross Entropy and Boundary-based Loss function were found to provide good results compared to other loss functions that were tested.

In implementation, the disclosed method of deriving initial TDM/BTM 150 may be introduced gradually, by adjusting weights given to straightforward computer vision derivation as the prior art method for deriving the TDM/BTM (CV—short for computer vision, e.g., $\beta$), to disclosed neural networks model (NN, or DNN 140, e.g., $\alpha$) and to their geometric average ($\sqrt{(CV \times NN)}$, e.g., $\gamma$), so that initial TDM/BTM 150 may be derived as $\alpha \cdot CV + \beta \cdot NN + \gamma \cdot \sqrt{(CV \times NN)}$, with weight $\alpha$ gradually decreased and weight $\beta$ gradually increased as the DNN model as we train it on more annotated data currently the optimized results were found to be in the following combination of—reaching, e.g., $\alpha=0.2$, $\beta=0.6$ and $\gamma=0.2$.

In certain embodiments, ultrasound registration module 101 may be further configured to accumulate the TDM/BTMs with respect to damage thresholds defined for frames from which the TDM/BTMs are derived. The TDM/BTMs may be processed as tissue damage probability maps, which may be weighted and/or processed with respect to specific thresholds assigned to specific frames—to yield the final TDM/BTM.

Figure 3:
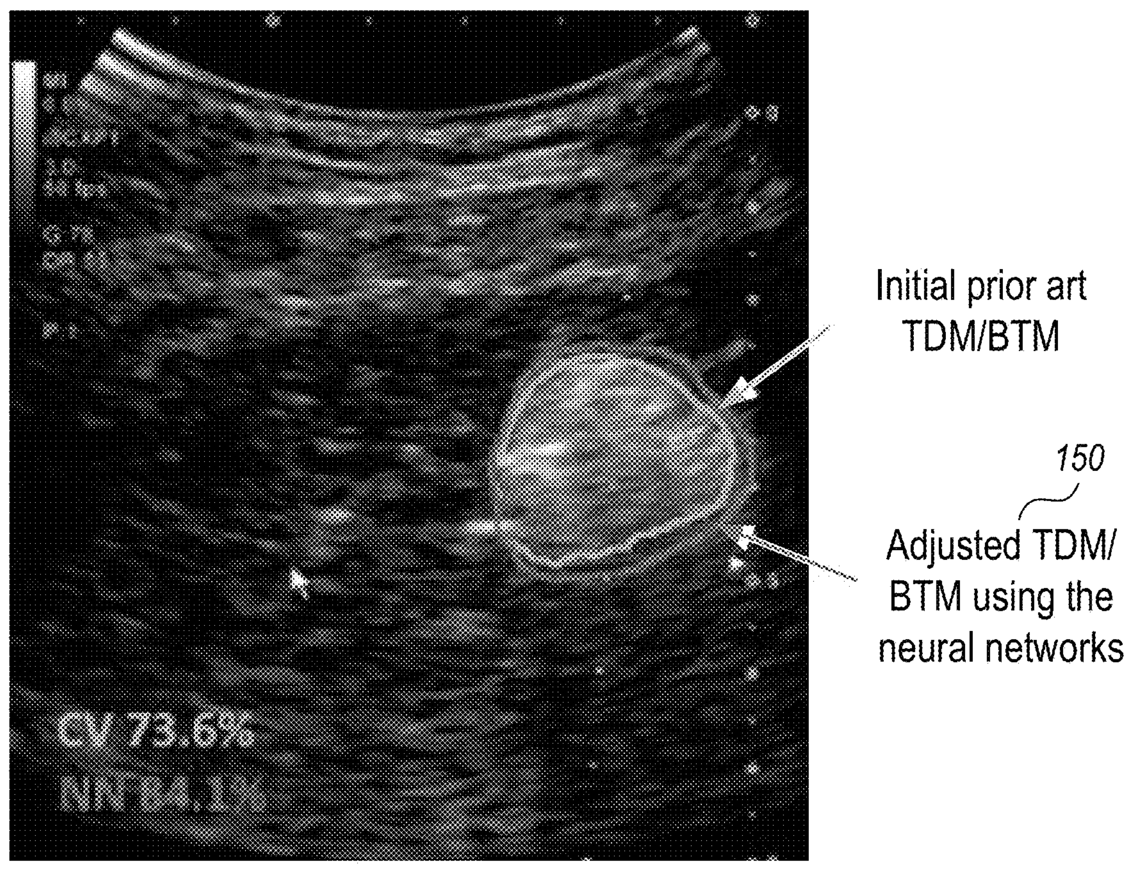
FIG. 3 provides a non-limiting example for the improvement provided by the disclosed methods, according to some embodiments of the invention.

FIG. 3 provides a non-limiting example for the improvement provided by the disclosed methods, according to some embodiments of the invention. A comparison is provided between the tissue damage maps calculated by prior art algorithms and tissue damage maps calculated using the disclosed approach implementing neural networks (initial TDM/BTMs 150). In the case of the non-limiting example, direct comparison with CT and/or MR data indicated an improvement of the dice score from 73.6% to 84.1% in the Sørensen-Dice coefficient using the disclosed algorithms, which practically halves the extent of mismatch between the TDM/BTM and the actual damage. This example shows that the disclosed methods are better than the prior art in detecting tissue damage, in particular in regions which are shadowed by emitted gas bubbles (e.g., when gas bubbles are positioned between the transducer and the damaged tissue).

Figure 4:
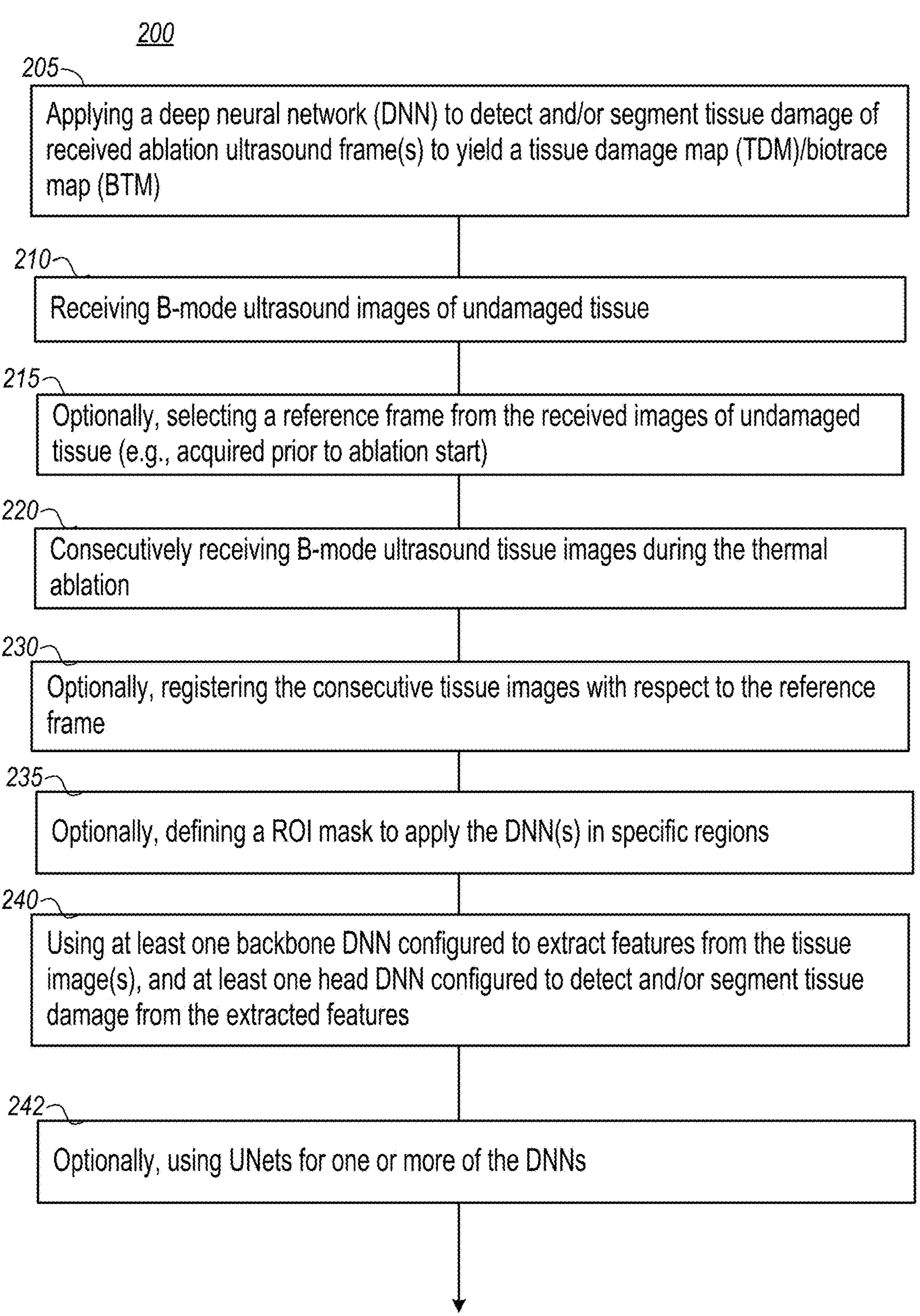
FIGS. 4 and 6 are high-level flowcharts illustrating methods, according to some embodiments of the invention.
Figure 4:
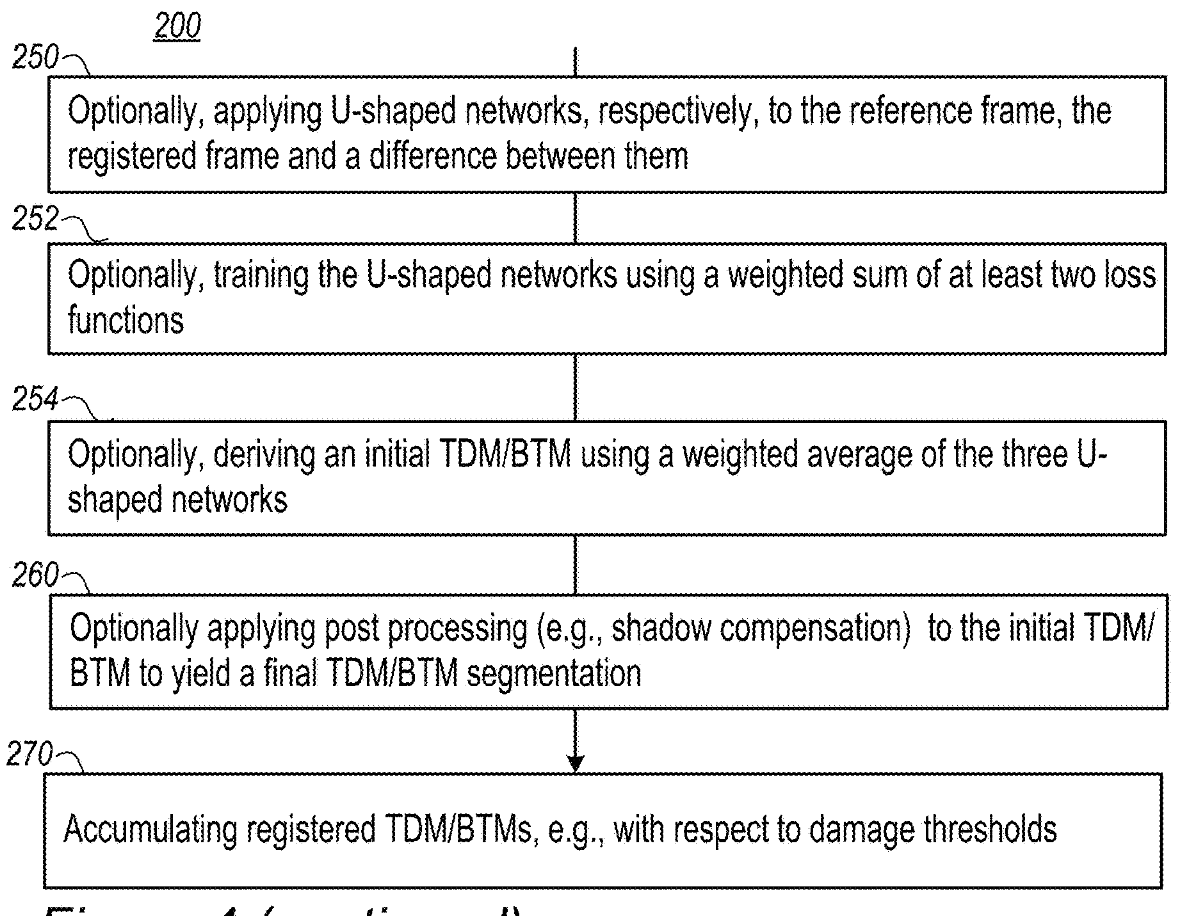

FIG. 4 is a high-level flowchart illustrating a method 200, according to some embodiments of the invention. The method stages may be carried out with respect to system 100 described above, which may optionally be configured to implement method 200. Method 200 may be at least partially implemented by at least one computer processor, e.g., in an ultrasound module such as ultrasound module 101. Certain embodiments comprise computer program products comprising a non-transitory computer readable storage medium having computer readable program embodied therewith and configured to carry out the relevant stages of method 200. Method 200 may comprise the following stages, irrespective of their order.

Method 200 comprises deriving a tissue damage map (TDM), also termed a biotrace map (BTM), during thermal ablation from ultrasound tissue images (e.g., B-mode images) by applying a deep neural network (DNN) to detect and/or segment tissue damage of a received ablation frame to yield the TDM/BTM (stage 205). Method 200 may comprise providing to the DNN, as input, a tissue image and optionally a reference image or a combination thereof, and deriving the TDM/BTM from the input tissue image. In various embodiments, the DNN may comprise one or more DNNs having U-shaped network (UNet) architectures.

In certain embodiments, method 200 may comprise receiving the B-mode ultrasound images of undamaged tissue (stage 210) as a warmup stage and consecutively receiving tissue B-mode ultrasound images during the thermal ablation (stage 220).

Method 200 may comprise deriving the TDM during thermal ablation from B-mode ultrasound tissue images, optionally by selecting a reference frame from received images of undamaged tissue (stage 215) and registering received tissue images during the thermal ablation with respect to the reference frame (stage 230); and accumulating the TDM/BTMs with respect to damage thresholds defined for frames from which the TDM/BTMs are derived (stage 270).

In various embodiments, reference frames may be used or not, and the TDM/BTM may be derived using one or more tissue damage images, optionally one or more reference images (e.g., captured before the ablation procedure starts) and any of the images may or may not be registered.

In some embodiments, method 200 may comprise defining a ROI mask to apply the DNN(s) in specific regions of the images (stage 235), to improve the accuracy and robustness of method 200, and specifically of the application of the DNNs (stage 205). For example, the ROI mask may be derived from the needle location or from specifications related to the ablation tool, and/or from information derived during the derivation of the TDM/BTM representations.

In various embodiments, method 200 may comprise using as the DNN at least one backbone DNN configured to extract features from the at least one tissue image, and at least one head DNN configured to detect and/or segment tissue damage from the extracted features (stage 240). Any one of the DNNs may comprise U-shaped networks (UNets) (stage 242).

Method 200 may further optionally comprise applying U-shaped networks, respectively, to the reference frame, the registered frame and a difference between them (stage 250). Certain embodiments comprise deriving an initial TDM/BTM using one or more DNNs, e.g., backbone DNN(s) and head DNN(s), which may be implemented in a non-limiting example by U-shaped networks, for example using a weighted average of three U-shaped networks applied, respectively, to the reference frame, the registered frame and a difference between them (stage 254), wherein the U-shaped networks are trained using a weighted sum of Binary Cross Entropy and Boundary-based Loss functions (stage 252). Method 200 may optionally comprise applying post processing and/or shadow compensation to the initial TDM/BTM to yield a final TDM/BTM segmentation (stage 260).

Corresponding computer readable program (see, e.g., executable code 64 in FIG. 5) may comprise one or more of the following, or part(s) thereof: computer readable program configured to receive images of undamaged tissue and consecutively receive tissue images during the thermal ablation—from an ultrasound image-guided system for thermal ablation, and computer readable program configured to derive therefrom a tissue damage map (TDM) or a biotrace map (BTM) by applying a deep neural network (DNN) to segment tissue damage of a received ablation frame to yield the TDM/BTM.

In certain embodiments, computer readable program may comprise computer readable program configured to select a reference frame from the received images of undamaged tissue and register consecutive received tissue images with respect to the reference frame, and computer readable program configured to apply the DNN to segment tissue damage of a registered ablation frame and yield the TDM/BTM. The DNN may receive as input a tissue image and optionally a reference image or a combination thereof, and the computer readable program may be configured to derive the TDM/BTM from the input tissue image.

In certain embodiments, the DNN may comprise at least one backbone DNN configured to extract features from the at least one tissue image, and at least one head DNN configured to detect and/or segment tissue damage, e.g., from the extracted features. One or more of the DNNs may comprise a U-shaped network (UNet).

In certain embodiments, computer readable program may comprise computer readable program configured to select a reference frame from received B-mode ultrasound tissue images of undamaged tissue, computer readable program configured to register received B-mode ultrasound tissue images during thermal ablation of the tissue, with respect to the reference frame, computer readable program configured to derive an initial tissue damage map (TDM) or a biotrace map (BTM) using one or more DNNs, e.g., backbone DNN(s) and head DNN(s), which may be implemented in a non-limiting example by a weighted average of three U-shaped networks applied, respectively, to the reference frame, the registered frame and a difference between them, wherein the U-shaped networks are trained using a weighted sum of Binary Cross Entropy and Boundary-based Loss functions, and optionally computer readable program configured to apply shadow compensation and post processing to the initial TDM/BTM to yield a final TDM/BTM segmentation.

In certain embodiments, computer readable program may comprise computer readable program configured to accumulate registered TDM/BTMs and derive an accumulated TDM/BTM therefrom, e.g., with respect to damage thresholds defined for frames from which the TDM/BTMs are derived.

Figure 5:
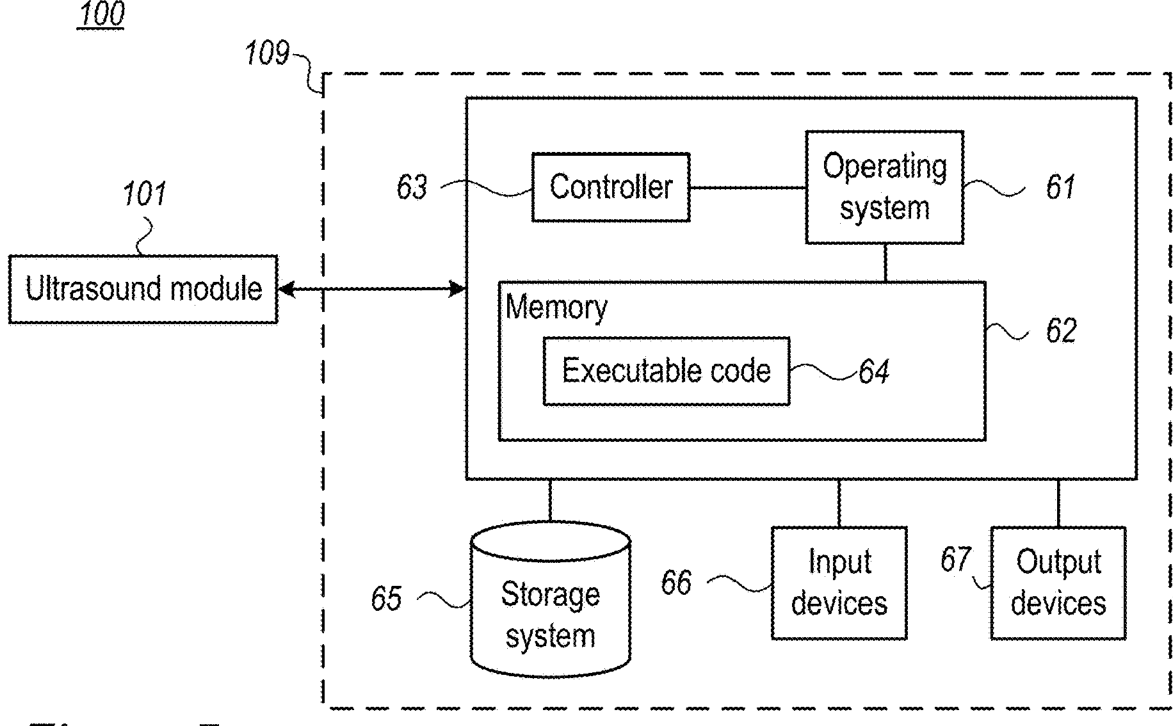
FIG. 5 is a high-level block diagram of an exemplary computing device, which may be used with embodiments of the present invention.

FIG. 5 is a high-level block diagram of exemplary computing device 109, which may be used with embodiments of the present invention. Computing device 109 may include a controller or processor 63 that may be or include, for example, one or more central processing unit processor(s) (CPU), one or more Graphics Processing Unit(s) (GPU or general purpose GPU-GPGPU), a chip or any suitable computing or computational device, an operating system 61, a memory 62, a storage 65, input devices 66 and output devices 67. Ultrasound module 101 may comprise at least parts of the computer system as shown for example in FIG. 5. Computer program products may comprise a computer readable storage medium such as memory 62 and/or storage 65, having computer readable program embodied therewith (e.g., executable code 64) and configured to carry out the relevant stages of method 200.

Operating system 61 may be or may include any code segment designed and/or configured to perform tasks involving coordination, scheduling, arbitration, supervising, controlling or otherwise managing operation of computing device 109, for example, scheduling execution of programs. Memory 62 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short-term memory unit, a long term memory unit, or other suitable memory units or storage units. Memory 62 may be or may include a plurality of possibly different memory units. Memory 62 may store for example, instructions to carry out a method (e.g., code 64), and/or data such as user responses, interruptions, etc.

Executable code 64 may be any executable code, e.g., an application, a program, a process, task or script. Executable code 64 may be executed by controller 63 possibly under control of operating system 61. For example, executable code 64 may when executed cause the production or compilation of computer code, or application execution such as VR execution or inference, according to embodiments of the present invention. Executable code 64 may be code produced by methods described herein. For the various modules and functions described herein, one or more computing devices 109 or components of computing device 109 may be used. Devices that include components similar or different to those included in computing device 109 may be used, and may be connected to a network and used as a system. One or more processor(s) 63 may be configured to carry out embodiments of the present invention by for example executing software or code.

Storage 65 may be or may include, for example, a hard disk drive, a floppy disk drive, a Compact Disk (CD) drive, a CD-Recordable (CD-R) drive, a universal serial bus (USB) device or other suitable removable and/or fixed storage unit. Data such as instructions, code, VR model data, parameters, etc. may be stored in a storage 65 and may be loaded from storage 65 into a memory 62 where it may be processed by controller 63. In some embodiments, some of the components shown in FIG. 5 may be omitted.

Input devices 66 may be or may include for example a mouse, a keyboard, a touch screen or pad or any suitable input device. It will be recognized that any suitable number of input devices may be operatively connected to computing device 109 as shown by block 66. Output devices 67 may include one or more displays, speakers and/or any other suitable output devices. It will be recognized that any suitable number of output devices may be operatively connected to computing device 109 as shown by block 67. Any applicable input/output (I/O) devices may be connected to computing device 109, for example, a wired or wireless network interface card (NIC), a modem, printer or facsimile machine, a universal serial bus (USB) device or external hard drive may be included in input devices 66 and/or output devices 67.

Embodiments of the invention may include one or more article(s) (e.g., memory 62 or storage 65) such as a computer or processor non-transitory readable medium, or a computer or processor non-transitory storage medium, such as for example a memory, a disk drive, or a USB flash memory, encoding, including or storing instructions, e.g., computer-executable instructions, which, when executed by a processor or controller, carry out methods disclosed herein.

Figure 6:
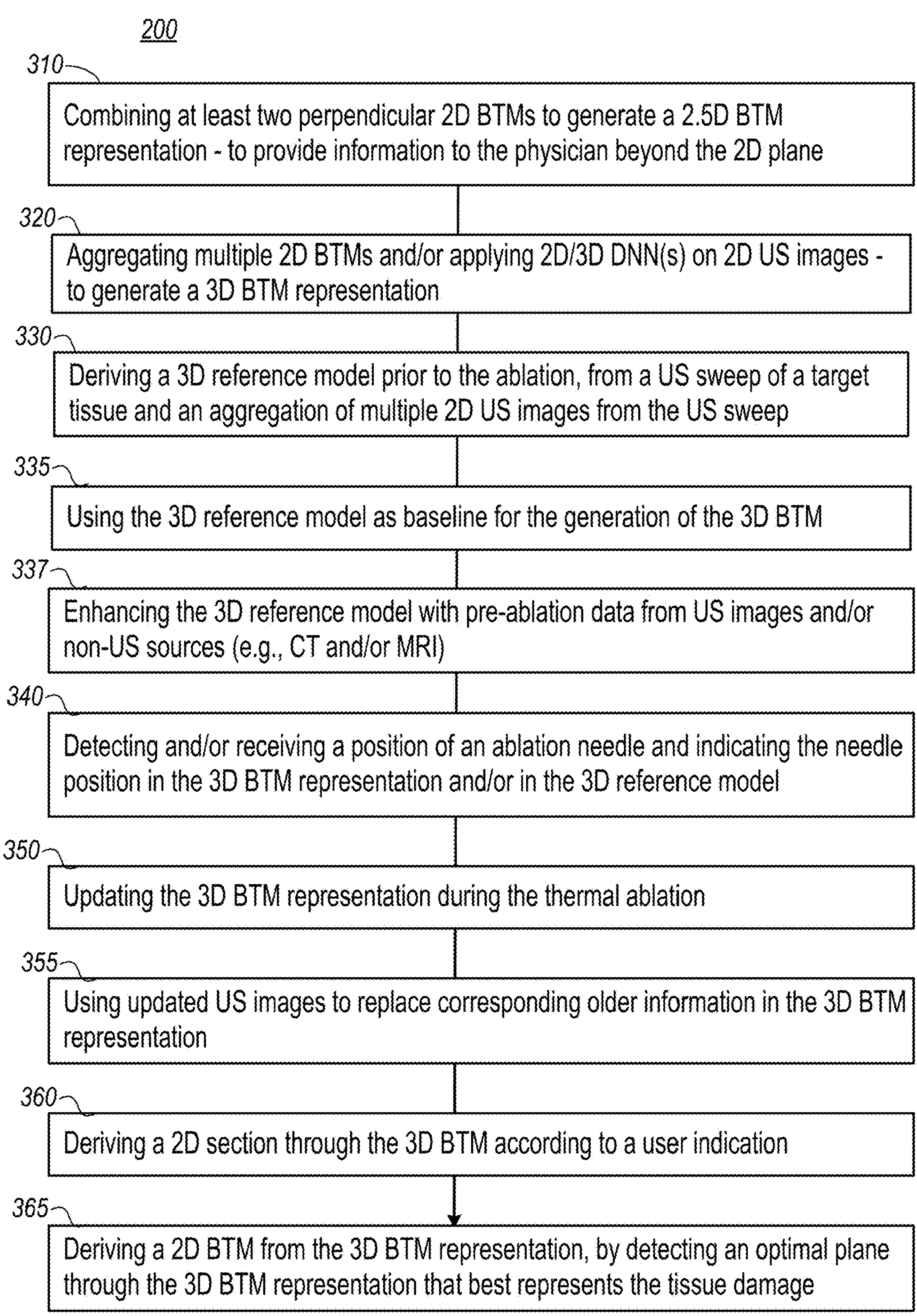

FIG. 6 is a high-level flowchart illustrating a method 200, according to some embodiments of the invention. The method stages may be carried out with respect to system 100 described herein, which may optionally be configured to implement method 200. Method 200 may be at least partially implemented by at least one computer processor, e.g., in an ultrasound module such as ultrasound module 101. Certain embodiments comprise computer program products comprising a non-transitory computer readable storage medium having computer readable program embodied therewith and configured to carry out the relevant stages of method 200. Method 200 may comprise stages described in FIG. 4 and/or the following stages, irrespective of their order.

Method 200 may comprise combining at least two perpendicular (or otherwise tilted with respect to each other) 2D BTMs to generate a 2.5D BTM representation, thus providing information to the physician beyond the 2D plane (stage 310). For example, a dual plane US probe may be used to yield two images from perpendicular planes (or planes tilted with respect to each other at an angle different from 90°) for each frame. Disclosed 2D algorithms may be run independently on each plane and synchronization between the BTM results for each plane may be carried out to ensure consistency along the line of intersection between the (e.g. perpendicular) planes.

Method 200 may comprise aggregating a plurality of 2D BTMs and/or 2D US images to generate a 3D BTM representation (stage 320), as disclosed herein. In various embodiments, one or more 2D and/or 3D DNNs may be applied to the aggregated US images to generate 3D BTMs.

Method 200 may further comprise deriving a 3D reference model prior to the ablation, from a US sweep of a target tissue and an aggregation of multiple 2D US images from the US sweep (stage 330); and further using the 3D reference model as baseline for the generation of the 3D BTM (stage 335). Method 200 may further comprise enhancing the 3D reference model with pre-ablation data from US images and/or from non-US sources (e.g., CT and/or MRI) (stage 337). It is noted that pre-ablation US images may be used to derive additional pre-ablation data, such as reference and/or patient anatomy data derived from 3D sweeps that may be processed to derive, e.g. for motion modeling, as more processing time is available for pre-ablation data.

Method 200 may further comprise detecting and/or receiving a position of an ablation needle and indicating the needle position in the 3D BTM representation and/or in the 3D reference model (stage 340). Alternatively or complementarily, the needle position may also be automatically detected or manually marked in 2D on one or more specific US frame image(s) and transformed to the 3D representation. For example, sweeping motions of the US probe, as explained herein, may be used to derive or integrate the location of the needle or parts thereof, especially across multiple oblique 2D images (with respect to the needle) during the sweeping. It is noted that the sweeping motions may but are not required to be gradual or continuous, as method 200 may derive the data from partial, brief, interrupted or spontaneous sweeping and not only from gradual sweeping.

Method 200 may further comprise updating the 3D BTM representation during the thermal ablation (stage 350), e.g., by using updated US images to replace corresponding older information in the 3D BTM representation (stage 355). For example, registration of the updated US images may be used to identify previous data that can be replaced with updated data, e.g., as the bubble cloud expands and the damage to the tissue accumulates.

Method 200 may further comprise deriving a 2D section through the 3D BTM according to a user indication (stage 360). Method 200 may further comprise deriving a 2D BTM from the 3D BTM representation, by detecting an optimal plane through the 3D BTM representation that best represents the tissue damage (stage 365). 2D section may comprise virtual US image(s) that may be derived from the 3D US volume and improve target visibility and monitoring accuracy. The 2D section may be derived from the US data and/or from the BTM representation.

Figure 7:
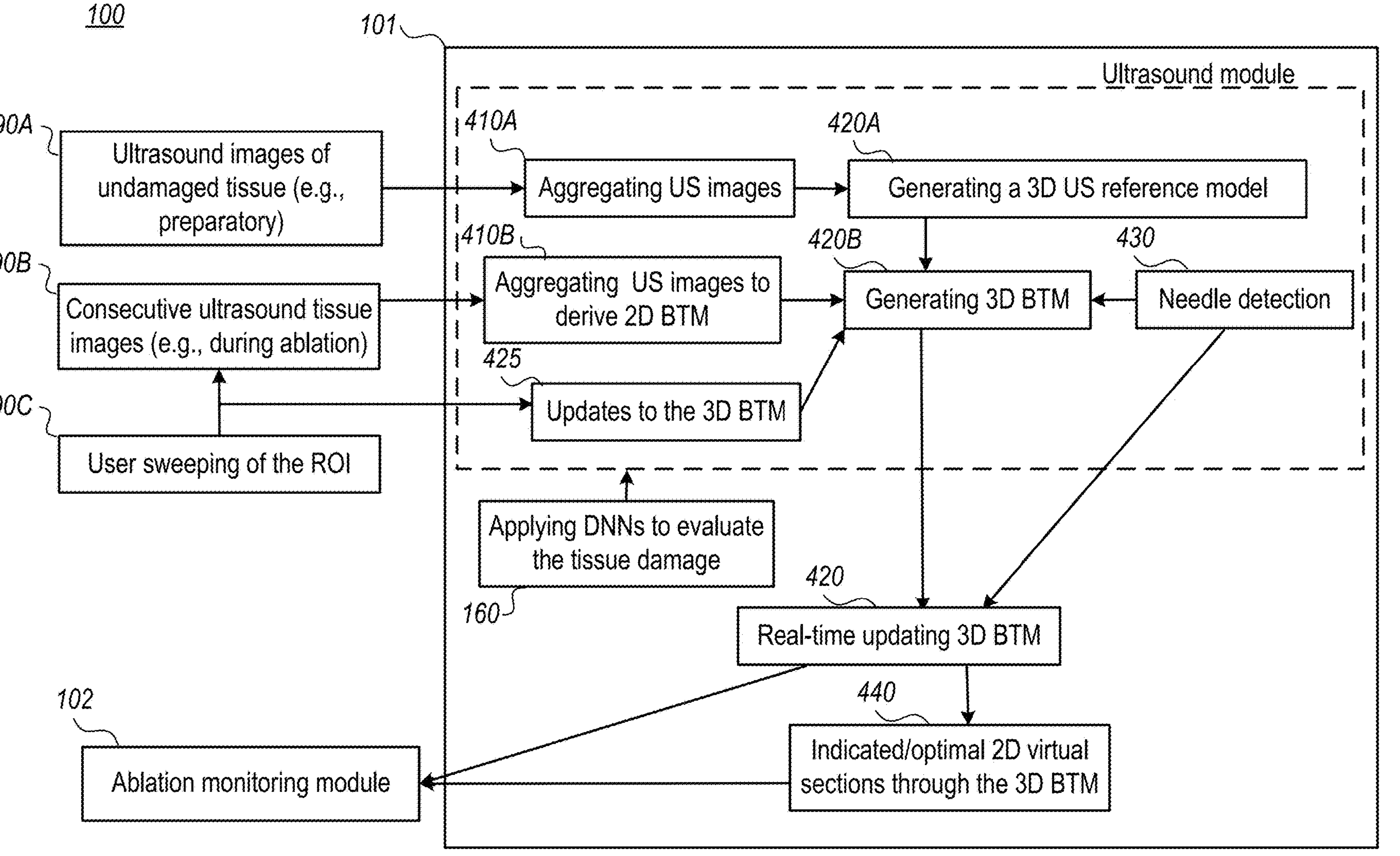
FIGS. 7 and 8 are high-level schematic block diagrams of non-limiting examples for ultrasound modules, according to some embodiments of the invention.
Figure 8:
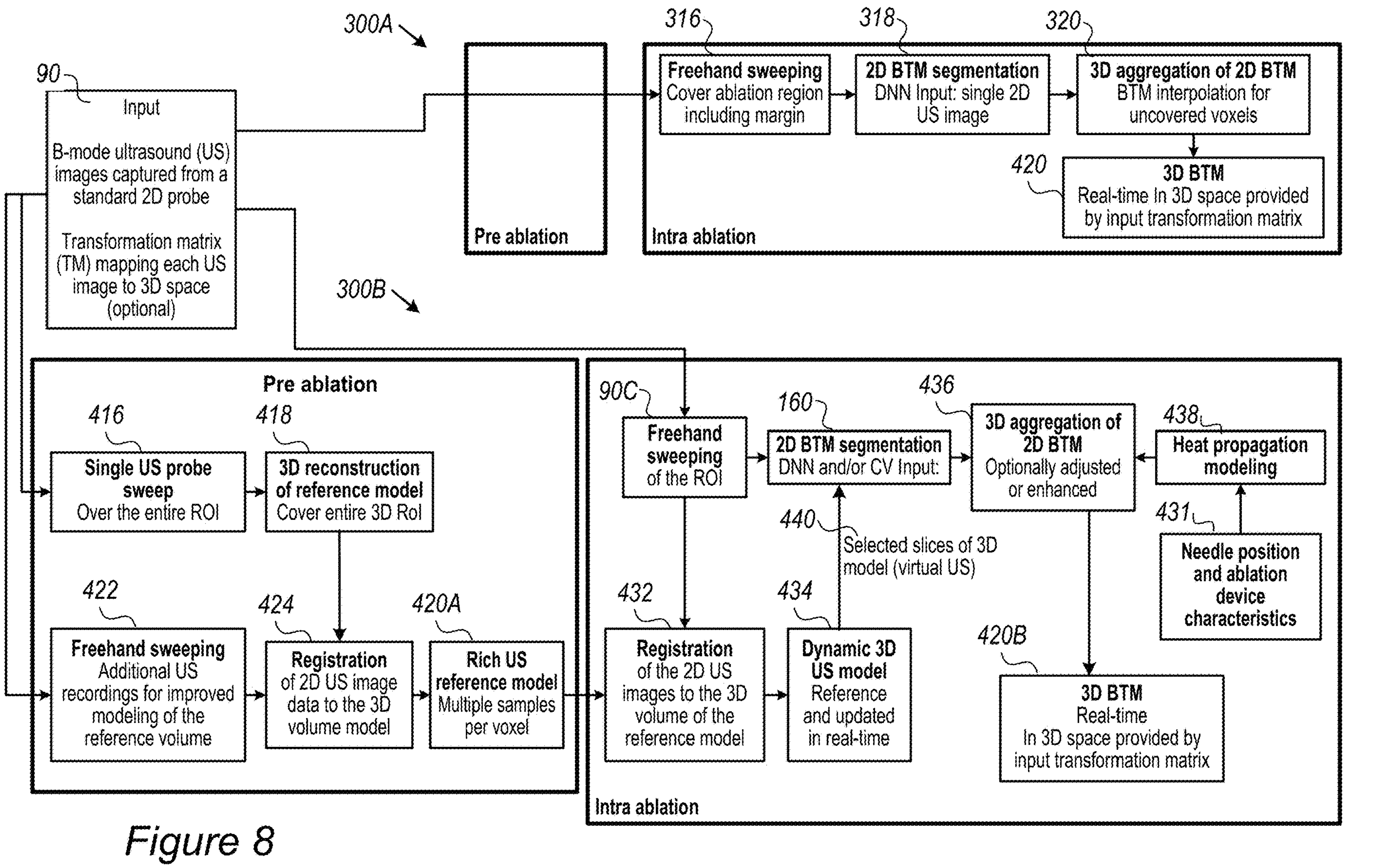

FIGS. 7 and 8 are high-level schematic block diagrams of non-limiting examples for ultrasound module 101, according to some embodiments of the invention. As illustrated schematically in FIG. 7, ultrasound module 101 in ultrasound image-guided system 100 for thermal ablation may be configured to aggregate a plurality of US images to derive 2D BTMs 410B from multiple US images 90B to generate a three-dimensional (3D) BTM representation 420B.

Optionally, prior to ablation, ultrasound module 101 may be configured to derive a 3D US reference model 420A from preparatory US images 90A, e.g., from a US sweep of a target tissue and an aggregation of multiple 2D US images 410A from the US sweep. 3D US reference model 420A may be further used as baseline for the generation of 3D BTM 420B during the ablation process.

In some embodiments, 3D reference model 420A may be enhanced with pre-ablation data from non-US sources (not shown) such as corresponding CT and/or MR (magnetic resonance) images onto which the US images are registered. For example, CT and/or MR images may be merged with the US data to yield an enhanced 3D reference model.

In some embodiments, ultrasound module 101 may monitor the generation of 3D reference model 420A and indicate if it is complete (e.g., filles a pre-defined ellipsoid volume at a given resolution), or if further sweeping is required to complete 3D reference model 420A-providing corresponding suggestions to the user in the preparation stage.

In some embodiments, ultrasound module 101 may provide indications or suggestions for sweeping directions or locations to overcome actual or potential shadowing of the tissue region ROI. Specifically in a pre-ablation stage, the user may be guided to achieve full volume representation in 3D reference model 420A, to prepare for and overcome potential distractive shadowing during the ablation procedure. Moreover, during the ablation stage, the user may also be guided to achieve full volume representation in 3D BTM model 420B, to achieve full coverage (or a required level of coverage) of the ROI during ablation, e.g., to overcome potential distractive shadowing and effects of the bubbles generated during the ablation procedure. The guidance may be provided as a feedback loop, during damage estimation, e.g., concerning unresolved regions in 3D BTM representation 420B.

In some embodiments, ultrasound module 101 may be further configured to detect or receive a position of an ablation needle 430 and indicate the needle position in 3D BTM representation 420B. Ultrasound module 101 is further configured to derive updates 425 to 3D BTM representation 420B during the thermal ablation, e.g., from US images received from a user sweeping the ROI 90C. 3D reference model 420A generated in the pre-ablation stage may be used as basis for deriving 3D BTM representation 420B during the thermal ablation.

Ultrasound module 101 may be further configured to update 3D BTM representation 420B during the ablation procedure, to yield a real time 3D BTM representation 420, which may be presented and processed during the ablation procedure to provide indications of the advancing ablation.

In some embodiments, ultrasound module 101 may be further configured to derive a 2D section 440 through 3D BTM 420 according to a user indication; and/or to derive a 2D BTM 440 from 3D BTM representation 420 by detecting an optimal plane through the 3D BTM representation that best represents the tissue damage.

In various embodiments, as indicated in a highly schematic manner in FIG. 7, any type of DNNs 160 may be applied to derive and/or update the corresponding BTM representation(s) from the corresponding US images by ultrasound module 101, as disclosed herein.

Ultrasound module 101 may be configured to derive the BTM representation in 2D, 2.5D and/or 3D, which may be provided to and analyzed by ablation monitoring module 102. 3D BTM representation may be provided in real-time to ablation monitoring module 102 and/or 3D BTM representation may be used to provide specific indications or derived indices that can be used by ablation monitoring module 102.

FIG. 8 schematically illustrates non-limiting details and examples for the operation of ultrasound module 101 and method 200, according to some embodiments of the invention. FIG. 8 schematically illustrates two algorithm versions for implementing ultrasound module 101 and method 200, a simpler algorithm 300A without pre-ablation preparation and with simplified generation of 3D BTM 420 during ablation; and a more complex algorithm 300B including multiple optional features, such as options for pre-ablation preparation and optional features that generate more accurate and/or more robust 3D BTM 420 during ablation.

Starting with input 90 to ultrasound module 101, which includes the B-mode US images captured using a standard 2D US probe and a transformation matrix (TM) which maps each US image to 3D space, simpler algorithm 300A uses free hand sweeping 316 by the user to cover the ablation region including margin (ROI—region of interest) to derive 2D BTM segmentation with a single 2D US image as the DNN input 318. The 2D BTMs are then aggregated 320 (e.g., using BTM interpolation for uncovered voxels) —to generate 3D BTM 420 which is constructed in real-time and in 3D space provided by the input transformation matrix.

Turning to a more complex algorithm 300B, an optional pre-ablation preparation may be carried out to derive reference model 420 as a rich US reference model, optionally with multiple samples per voxel (that can be modelled, e.g., by the mean and standard deviation of the parameters, or by any other setting). Input 90 may be used to derive from a single US probe sweep 416, which covers the entire ROI and is carried out, e.g., preferably during a breath hold or after an exhale—to generate a 3D reconstruction of reference model 418 that covers the entire 3D ROI. Reference model 418 may be used by the BTM segmentation of each frame (CV or DNN) to help detect the gas bubbles during ablation by comparing the frame image with the corresponding image before ablation started. In some embodiments, reference model 418 may further be enhanced by additional US recordings and data for improved modeling of the reference volume, e.g., including breathing motion, which may be derived, e.g., from the 30 sec freehand sweeping 422 followed by registration 424 (e.g., rigid (affine) registration or deformable registration) of the 2D US image(s) to 3D volume reference model 418, optionally compensating for detected motions or detected inaccuracies in input TM 90.

During ablation, algorithm 300B may receive US images from the user freehand sweeping 90C of the ROI to cover the ablation region including a margin—which are registered 432 onto reference model 420A (e.g., implementing rigid (affine) registration or deformable registration), optionally compensating for motion or input TM inaccuracies. US images 90C may be further used as input to implement a DNN to derive 2D BTM segmentation 160 as described herein and/or CV Input (computer vision input) to yield a single 2D US image (real or virtual) and optionally a reference image (optional). It is noted that in this context, CV refers to a per-frame BTM segmentation algorithm that does not use machine learning (e.g., DNN) as disclosed herein. In a simplified version CV input compares the current image with the reference image and identifies the brighter pixels.

In some embodiments, received B-mode US images captured using a standard 2D US probe may be stitched together to derive a consistent 3D representation by algorithm 300A or 300B, without access to tracking transformation such as TM matrix.

The derivation of 2D BTM segmentation 160 may be enhanced by a dynamic 3D US model 434 derived from registration 432. Dynamic 3D US model 434 may be initialized as a reference and be updated in real-time. Selected slices of the 3D model 440 may be used as virtual US images to enhance segmentation and/or for presentation to the user (physician) carrying out the ablation procedure. 2D BTM segmentations 160 may then be aggregated to yield a 3D aggregation model 436, optionally with weights assigned to the 2D BTM segmentations, e.g., by a heat propagation model 438 (evaluating, e.g., the propagation of heat through the tissue, see, e.g., numeral 82 in FIG. 1) and optionally interpolating BTM for uncovered voxels. Non-limiting examples for heat propagation modeling 438 may comprise DNN and/or CV input such as a single 2D US image and optionally a reference image; and may utilize information concerning the needle position and ablation device characteristics 431, based, e.g., on manual and/or automatic needle detection 430 (see FIG. 7), as well as data such as the type of the device, the energy settings, etc.

FIGS. 9A-9F provide non-limiting examples of ways of ultrasound imaging and scanning a region of interest (ROI) 83, according to some embodiments of the invention. Advantageously, disclosed embodiments are able to use sweeping motions, which are typically performed by the user (physician) to obtain an overview of the ROI—to generate and update the complete 3D US model, including the 3D BTM. In various embodiments, ROI mask may be applied to optimize the performance of the DNNs, e.g., an ROI mask covering ROI 83. In a non-limiting example, the ROI mask may be derived from the needle location and from needle operative specifications.

Figures 9A, 9B, 9C:
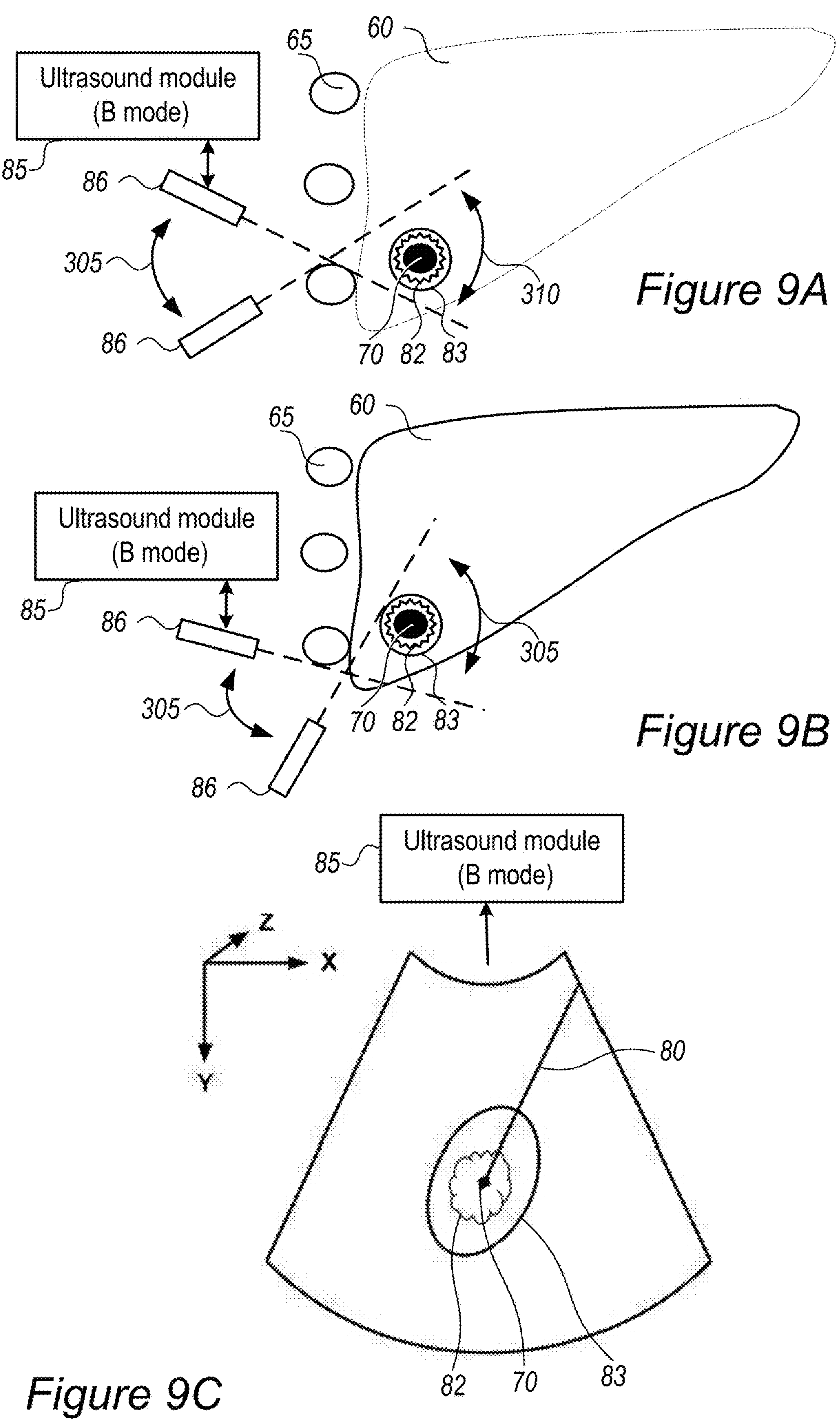
FIGS. 9A-9F provide non-limiting examples of ways of ultrasound imaging and scanning a region of interest (ROI), according to some embodiments of the invention.

FIGS. 9A and 9B schematically illustrate a liver 60 and two different options for using US probe 86 to scan ROI 83, including a tissue target 70 (e.g., a tumor) and ablation region 82. It is noted that depending on the position of the ROI in the liver, ribs 65 may present a significant obstacle to US imaging by generating shadow of the ribs that may obscure parts of the ROI—requiring US imaging to be carried out between ribs 65 (FIG. 9A) or beneath ribs 65 (FIG. 9B), depending on the position of the tissue target 70. Schematic ranges of available sweeping are indicated by numeral 305. Disclosed methods may at least partly overcome this limitation by maintaining the 3D US model of ROI 83, accumulating the best available information and reducing the effect of shadowing. Advantageously, disclosed methods utilize regular US probe 86 (rather than dedicated 3D US probes), which is relatively small and maximizes the available imaging volume. Moreover, advantageously, using regular US probe 86 is simpler, cheaper and more available to the user (e.g., physician) and enable regular manipulation (e.g., sweeping) of US probe 86, with disclosed methods 200 and US module 101 deriving the 3D model from the 2D B mode US images.

FIG. 9C-9F demonstrate US imaging modes—FIG. 9C illustrates schematically a base plane view, including full view of needle 80, target 70 (e.g., tumor) ablation zone 82 and ROI 83, as imaged in an ideal setting. While it is difficult to maintain or even achieve such view during the ablation procedure, disclosed 3D volume reference model 418 may be derived from initial pre-ablation images and/or 3D real-time model 420 may be derived from real-time intra-ablation images—to provide a full view of the ROI even when no single US image is available to provide such complete view. For example, 3D volume reference model 418 may be derived by maintaining the full view in the xy plane illustrated in FIG. 9C, and gradually tilting the US probe in the z direction to generate 3D volume reference model 418.

Figure 9F:
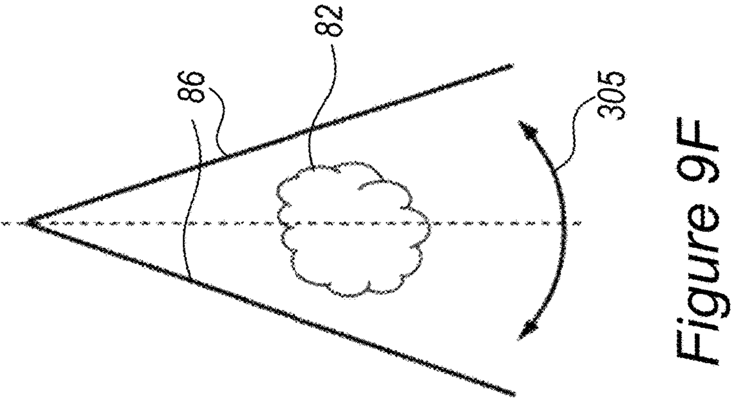
Figure 9E:
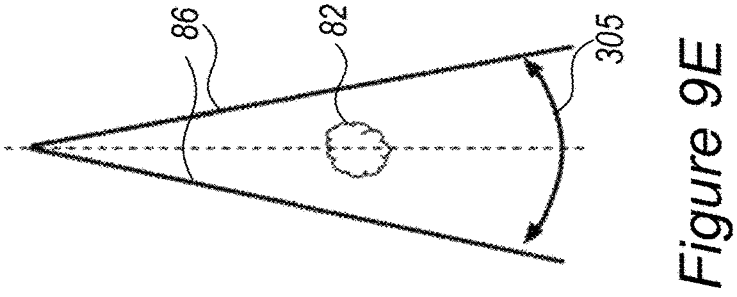
Figure 9D:
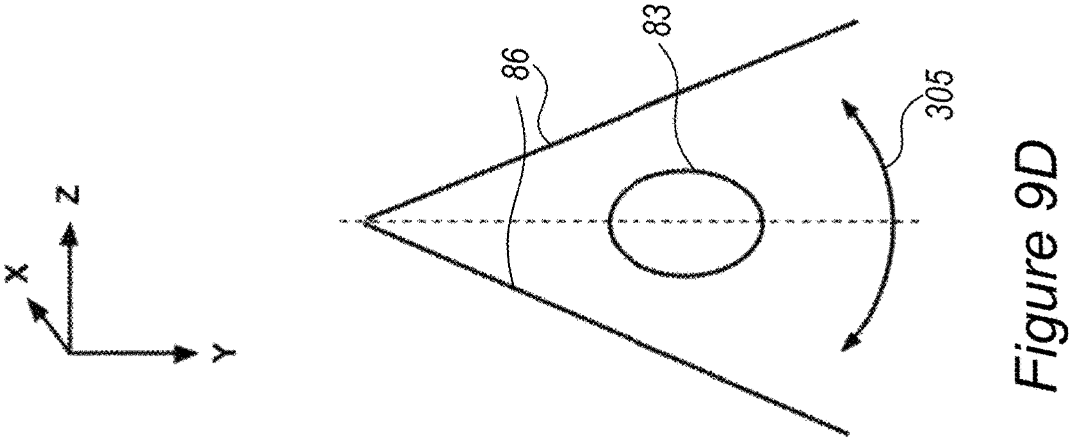

FIGS. 9D-9F schematically illustrate perpendicular views that illustrate sweeping angles 305 for US probes 86 that may be used to 3D volume reference model 418—e.g., by a relative broad sweep (FIG. 9D) intended to cover ROI 83 and areas on its sides in a preparatory stage, and then a narrow sweep of ablation region 82 (FIG. 9E), which gradually expands as the ablation procedure advances and ablation zone 82 expands (FIG. 9F). Including marginal areas allows to maintain full 3D real-time model 420 and update 3D real-time model 420 during the ablation procedure as required.

It is noted that the pre-ablation sweep is advantageous when covering the whole volume of the ROI, while US imaging during the ablation may be partial, with the US module and method updating the 3D model as required-leaving the user with maximal flexibility to move the US probe around as required by the procedure. In some embodiments, the US module and method may be configured to deliver an alert if relevant regions in or in proximity to the ROI have not been scanned for specified periods, or in case the ablation region nears specific regions which are not up to date.

Figure 10A:
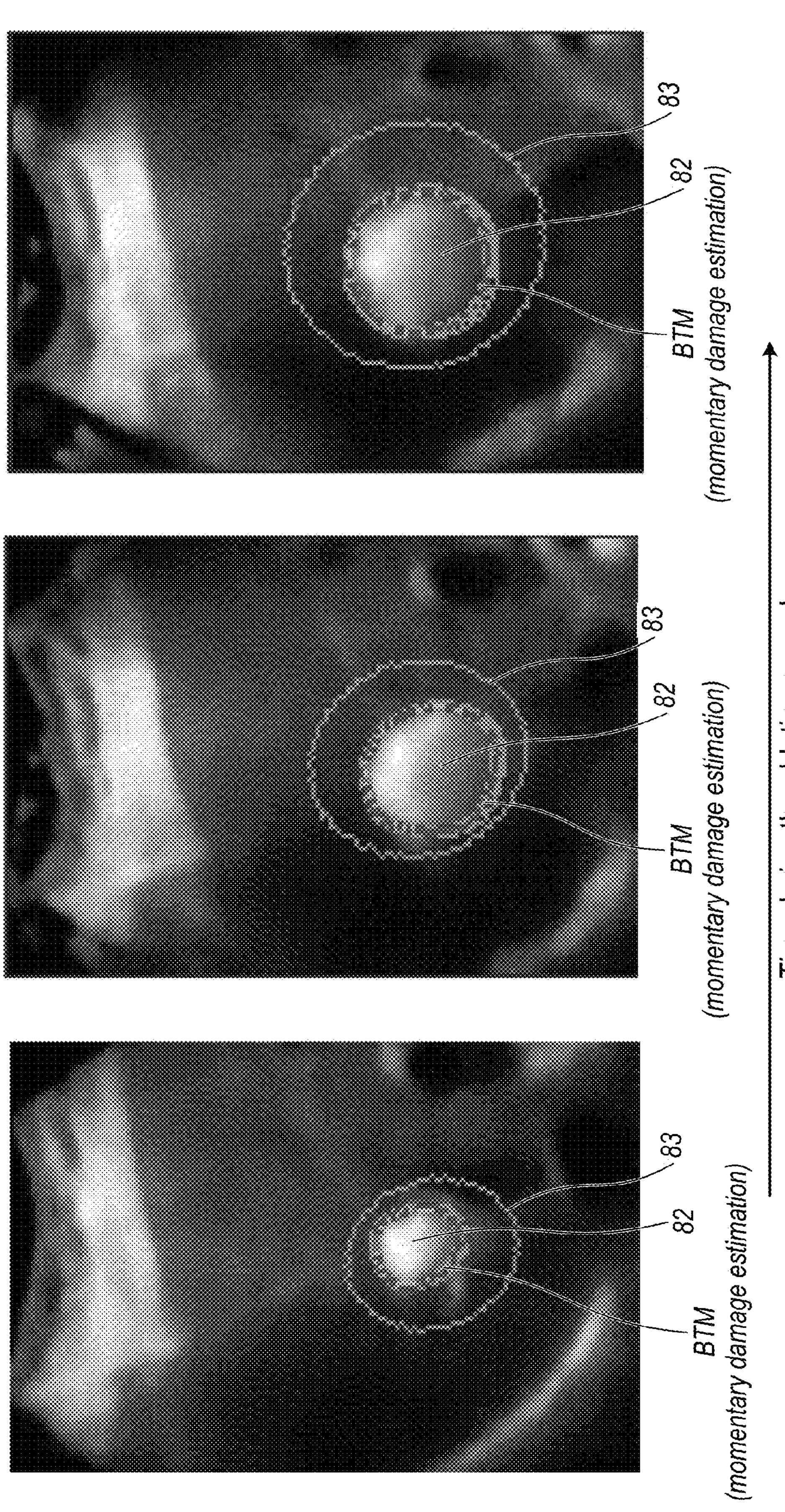
FIGS. 10A-10C provide experimental results indicating the efficiency of tissue damage estimation by the disclosed methods and US modules, according to some embodiments of the invention.
Figure 10B:
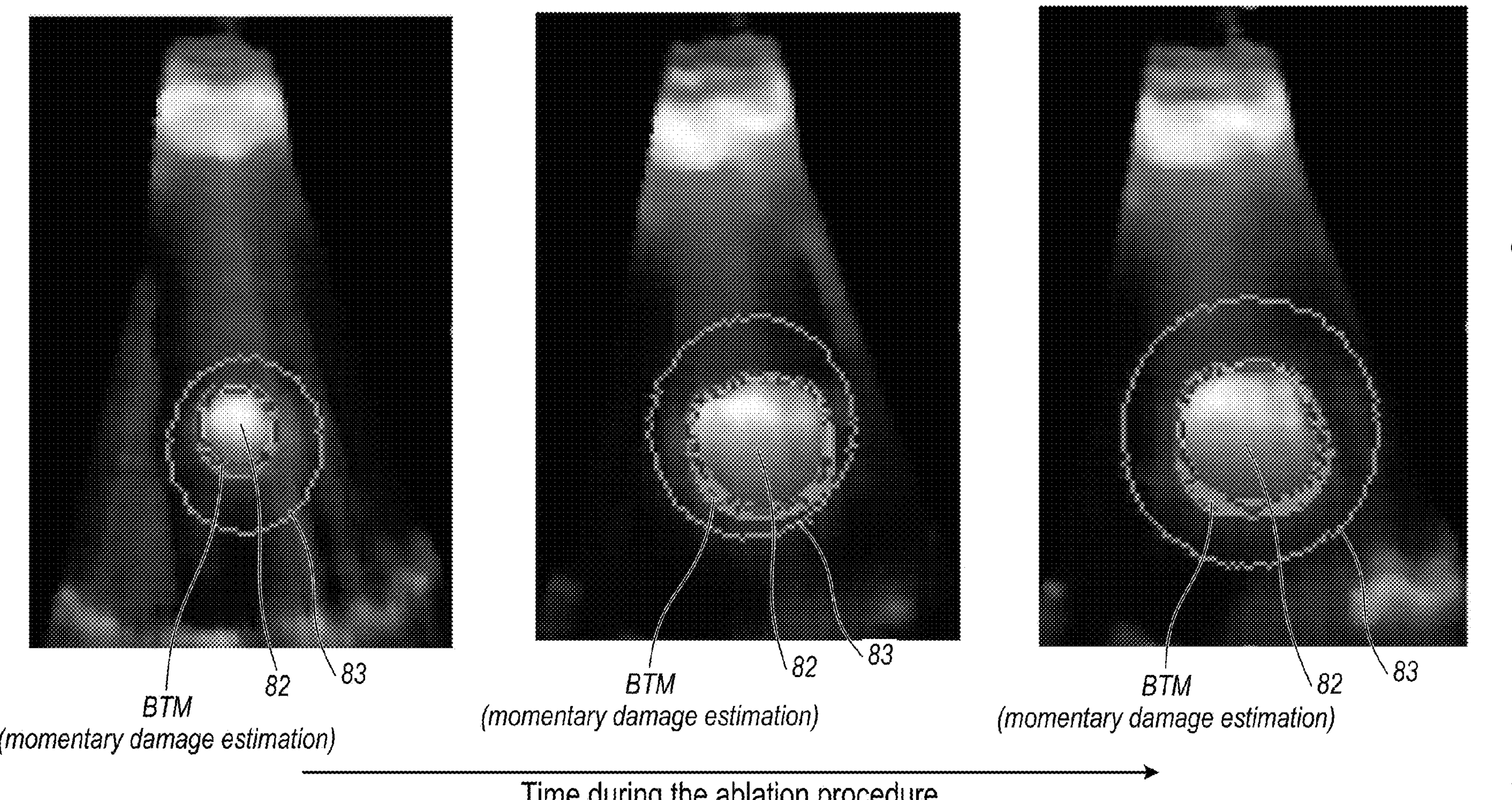
Figure 10C:
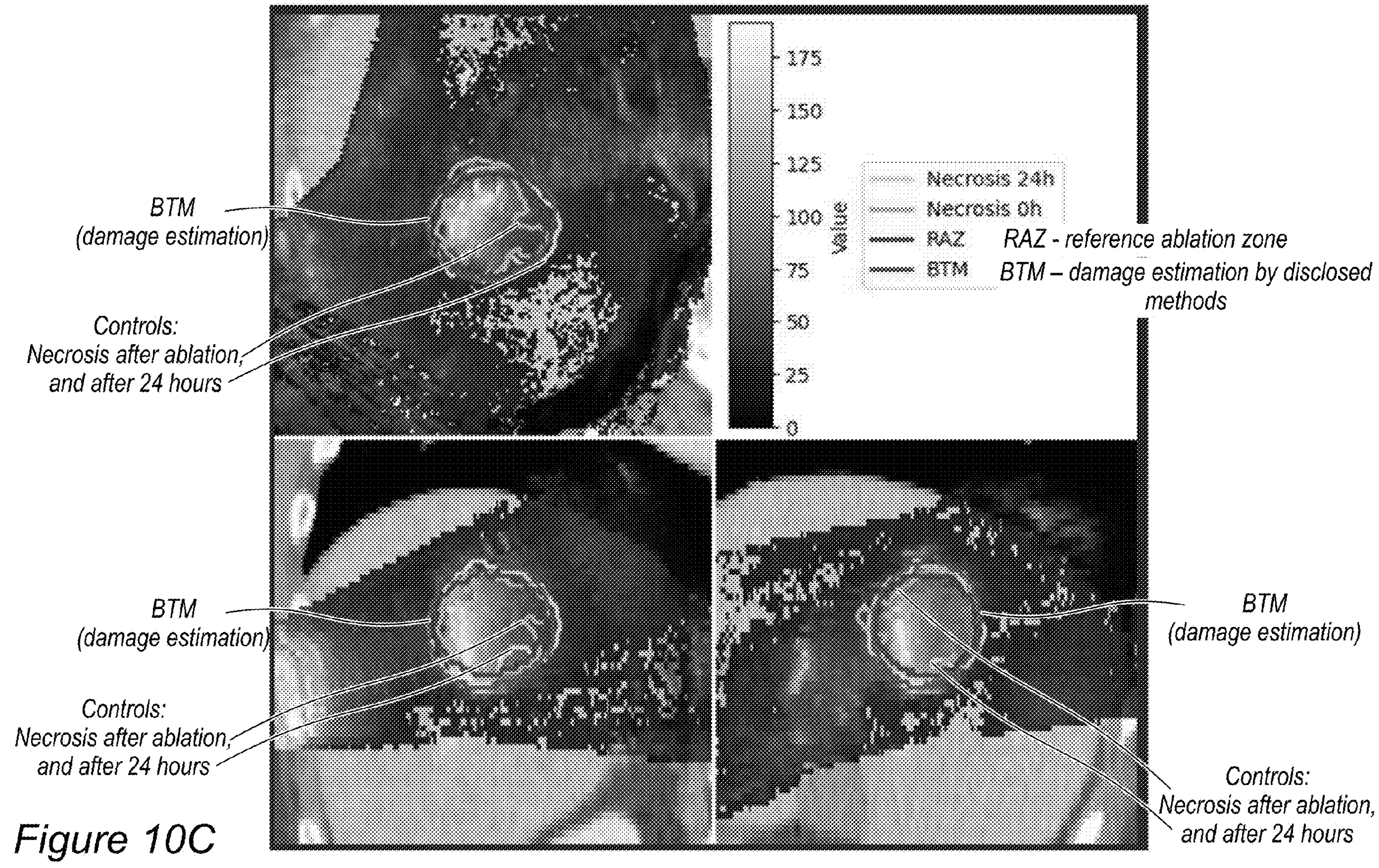

FIGS. 10A-10C provide experimental results indicating the efficiency of tissue damage estimation by the disclosed methods and US modules, according to some embodiments of the invention.

FIGS. 10A and 10B illustrate examples for virtual US images derived during ablation from 3D real-time model 420, onto which ROI 83 and ablation region 82 are marked, and the current BTM is annotated, providing the momentary damage estimation. FIGS. 10A and 10B provide virtual US images from two different directions which are derived from 3D real-time model 420 to illustrate the possibility of choosing a specific plane as a slice for the presentation. It is noted that the virtual US images, or slices, derived from 3D real-time model 420 may be at one or more planes, selected by the user or optimized to show best views of the ablation procedure by disclosed US module and methods. In some embodiments, a large number of virtual 2D US images may be derived from the 3D US model, e.g., a few tens of images centered on the ablation target and rotating around it to cover the volume of the treated area, and DNN may be applied to all virtual images to evaluate the created ablation damage as the 3D BTM.

Advantageously, disclosed one or more virtual US images may be located within the 3D volume to provide optimal information concerning the tissue damage. Optimizing the planes of the virtual US image(s) provide more accurate information concerning tissue damage than an obtained US image in a manually selected plane, as the latter may lack some of the required information. Furthermore, the combination of sweeping disclosed herein and the generation of virtual US images may enable better monitoring of the ablation boundaries, ensuring no unintended damage is inflicted on healthy tissue or adjacent elements (organs, vessels, nerves, etc.).

FIG. 10C provides an example for the accuracy of the disclosed BTM estimation, compared with the necrosis region immediately after the ablation procedure, and with the necrosis regions after 24 hours. The values indicated in color in the figures are LUT (look-up table) values derived from the US image. It is clear that the disclosed BTM estimation agrees well with the latter evaluation-thus providing in real time a better estimation than is actually seen in the former evaluation, and corresponding to the actual damage, which in the prior art requires time and additional imaging to achieve. It is noted that the disclosed BTM estimation was also found to be more accurate than the ablation device baseline estimation (denoted RAZ-reference ablation zone). The great advantage of disclosed evaluations is that they are accurate and in real-time-thus enabling the physician to correct and adjust the thermal ablation procedure in real time (e.g., adjust ablation parameters such as duration, or re-position the needle during the procedure itself), under consideration of the damage as would be observed a day after the procedure-anticipating full removal of the target tissue (e.g., a tumor) with minimal damage to surrounding healthy tissue.

Currently, based on 14 clinical and 4 pre-clinical cases in which the disclosed methods and US modules have been implemented, the BTM estimation was found to correspond to the evaluation of necrosis after 24 hours. Table 1 provides comparative accuracy indices for the disclosed evaluation methods compared to prior art evaluations. It is noted that these results are of an initial version of the disclosed algorithm and the accuracy is expected to increase as the algorithm is improved in updated versions and is trained on more data. These initial results indicate that disclosed methods provide significant improvements over prior art methods, as explained herein.

TABLE 1 comparative accuracy indices

| | | Prior art evaluation methods | |
|---|---|---|---|
| | BTM compared to necrosis after 24 h | Necrosis at 0 h compared to 24 h | RAZ compared to necrosis after 24 h |
| Mean Dice overlap metric | 0.73 | 0.75 | 0.64 |
| Median surface distance (mm) | 2.4 | 2.3 | 3.7 |
| Hausdorff surface distance (mm) | 12.6 | 10.8 | 13.0 |
| Mean relative volume error | 18.5% | −27.3% | −33.5% |
| Mean of absolutes of the relative volume error | 29.9% | 27.3% | 38.6% |

As indicated in Table 1, disclosed BTM evaluations are equivalent and provide in real time similar estimations as the necrosis measurement right after the procedure (which require separate imaging after the ablation procedure has ended, such as invasive CT imaging, applying radiation with a contrast agent) compared to the current baseline measure of evaluating the thermal ablation procedure after 24 hours. Disclosed BTM evaluations were also found to be more accurate than estimations provided in real time by the ablation device (RAZ). Initial results indicate that the BTM accuracy may be increased to around 0.8 mean Dice overlap metric, making disclosed BTM evaluations even more accurate and better corresponding to the actual resulting tissue damage (after 24 h) and put it in the range of inter-observer variability of manual annotation of the damage in CT images (see, e.g., Covert et al. 2022, Intra- and Inter-operator variability in manual tumor segmentation: Impact on radionuclide therapy dosimetry, Journal of Nuclear Medicine August 2022, 63 (supplement 2) —reporting Dice 0.79 for inter-observer variability vs. Dice 0.85 for intra-observe).

Elements from FIGS. 1-10C may be combined in any operable combination, and the illustration of certain elements in certain figures and not in others merely serves an explanatory purpose and is non-limiting.

Aspects of the present invention are described above with reference to flowchart illustrations and/or portion diagrams of methods, apparatus (systems) and computer program products according to embodiments of the invention. It will be understood that each portion of the flowchart illustrations and/or portion diagrams, and combinations of portions in the flowchart illustrations and/or portion diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or portion diagram or portions thereof.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or portion diagram or portions thereof.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or portion diagram or portions thereof.

The aforementioned flowchart and diagrams illustrate the architecture, functionality, and operation of possible implementations of systems, methods and computer program products according to various embodiments of the present invention. In this regard, each portion in the flowchart or portion diagrams may represent a module, segment, or portion of code, which comprises one or more executable instructions for implementing the specified logical function (s). It should also be noted that, in some alternative implementations, the functions noted in the portion may occur out of the order noted in the figures. For example, two portions shown in succession may, in fact, be executed substantially concurrently, or the portions may sometimes be executed in the reverse order, depending upon the functionality involved. It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. An ultrasound module in an ultrasound image-guided system for thermal ablation, the ultrasound module configured to receive at least one B-mode ultrasound (US) tissue image during the thermal ablation, and to derive therefrom a biotrace map (BTM) that provides a tissue damage assessment—by applying at least one deep neural network (DNN) to segment tissue damage in the at least one received tissue image to yield the BTM, wherein:

the DNN has a U-shaped network (UNet) architecture, the DNN is derived from a weighted average of three U-shaped networks applied, respectively, to a reference frame, a registered frame and a difference between them, and the U-shaped networks are trained using a weighted sum of at least two loss functions.

2. The ultrasound module of claim 1, wherein the at least one B-mode US tissue image comprises a plurality of two-dimensional (2D) US images and wherein the ultrasound module is further configured to aggregate a plurality of the 2D US images to generate a three-dimensional (3D) BTM representation.

3. The ultrasound module of claim 2, further configured to derive at least one virtual 2D section through the 3D BTM representation according to a user indication, to optimize target visibility and damage estimation in addition to the received at least one B-mode US image.

4. The ultrasound module of claim 2, further configured to detect or receive a position of an ablation needle and indicate the needle position in the 3D BTM representation.

5. The ultrasound module of claim 2, further configured to derive a 3D reference model prior to the ablation, from a US sweep of a target tissue and an aggregation of multiple 2D US images from the US sweep; wherein the 3D reference model is further used as baseline for the generation of the 3D BTM.

6. The ultrasound module of claim 5, further configured to enhance the 3D reference model with pre-ablation data from additional image modalities including CT (computer tomography) and/or MR (magnetic resonance).

7. The ultrasound module of claim 5, further configured to detect or receive a position of an ablation needle and indicate the needle position in the 3D reference model.

8. The ultrasound module of claim 2, further configured to update the 3D BTM representation during the thermal ablation.

9. The ultrasound module of claim 2, further configured to derive a 2D BTM from the 3D BTM representation, by detecting an optimal plane through the 3D BTM representation that best represents the tissue damage.

10. The ultrasound module of claim 2, further configured to derive a 3D BTM representation with 3D tissue damage estimation from the US images by applying the at least one DNN.

11. The ultrasound module of claim 1, further configured to receive at least one reference image and derive the BTM with respect thereto, wherein the at least one reference image comprises at least one image of undamaged tissue.

12. The ultrasound module of claim 11, further configured to derive the BTM by:

selecting a reference frame from the at least one image of undamaged tissue, registering consecutive at least one received tissue image with respect to the reference frame, to yield a registered ablation frame, and applying the DNN to segment tissue damage of the registered ablation frame to yield the BTM, wherein the DNN is two dimensional (2D) or three dimensional (3D).

13. The ultrasound module of claim 1, wherein the DNN comprises at least one backbone DNN configured to extract features from the at least one tissue image, and at least one head DNN configured to detect and/or segment tissue damage from the extracted features.

14. The ultrasound module of claim 1, wherein the DNN is applied within a defined ROI (region of interest) mask selected to improve the accuracy and robustness.

15. The ultrasound module of claim 1, wherein the at least two loss functions comprise Binary Cross Entropy and Boundary-based Loss functions.

16. The ultrasound module of claim 1, further configured to accumulate multiple registered BTMs and derived an accumulated BTM therefrom.

17. The ultrasound module of claim 1, further configured to accumulate multiple BTMs with respect to damage thresholds defined for frames from which the BTMs are derived.

18. The ultrasound module of claim 1, further configured to apply shadow compensation and post processing to the BTM to yield a final BTM segmentation.

19. An ultrasound image-guided system for thermal ablation, the system comprising an ultrasound module operable in the ultrasound image-guided system, the ultrasound module configured to receive at least one B-mode ultrasound (US) tissue image during the thermal ablation, and to derive therefrom a biotrace map (BTM) that provides a tissue damage assessment—by applying at least one deep neural network (DNN) to segment tissue damage in the at least one received tissue image to yield the BTM, wherein:

the DNN has a U-shaped network (UNet) architecture, the DNN is derived from a weighted average of three U-shaped networks applied, respectively, to a reference frame, a registered frame and a difference between them, and the U-shaped networks are trained using a weighted sum of at least two loss functions.

20. A method comprising deriving a biotrace map (BTM) during thermal ablation from at least one B-mode ultrasound (US) tissue image received during the thermal ablation by applying at least one deep neural network (DNN) to segment tissue damage in the at least one received ultrasound tissue image, wherein:

the DNN has a U-shaped network (UNet) architecture, the DNN is derived from a weighted average of three U-shaped networks applied, respectively, to a reference frame, a registered frame and a difference between them, and the U-shaped networks are trained using a weighted sum of at least two loss functions.

21. The ultrasound module of claim 4, configured to update the 3D BTM representation with derived data concerning heat propagation with respect to the needle position.

22. The ultrasound module of claim 7, further configured to update the 3D BTM representation with derived data concerning heat propagation with respect to the needle position.

* * * * *